United States Patent [19]

Jeffries et al.

[11] Patent Number: 5,369,024
[45] Date of Patent: Nov. 29, 1994

[54] XYLANASE FROM STREPTOMYCES ROSEISCLEROTICUS NRRL-11019 FOR REMOVING COLOR FROM KRAFT WOOD PULPS

[75] Inventors: Thomas W. Jeffries; Anthony C. Grabski; Rajesh N. Patel, all of Madison, Wis.

[73] Assignee: The United States of America as represented by the Secretary of Agriculture, Washington, D.C.

[21] Appl. No.: 857,060

[22] Filed: Mar. 25, 1992

[51] Int. Cl.$^5$ .......................... C12N 9/24; C12N 1/20
[52] U.S. Cl. .................. 435/200; 435/253.5; 435/886
[58] Field of Search ............... 435/200, 886, 253.5

[56] References Cited

U.S. PATENT DOCUMENTS

| | | | |
|---|---|---|---|
| 4,687,741 | 9/1987 | Farrell et al. | 435/189 |
| 4,687,745 | 9/1987 | Farrell et al. | 435/278 |
| 4,690,895 | 9/1987 | Farrell et al. | 435/278 |
| 4,692,413 | 9/1987 | Farrell et al. | 435/278 |
| 4,725,544 | 2/1988 | Tan et al. | 435/200 |
| 4,950,597 | 8/1990 | Saxena et al. | 435/101 |
| 4,966,850 | 10/1990 | Yu et al. | 435/200 |

FOREIGN PATENT DOCUMENTS

| | | |
|---|---|---|
| 0261080 | 3/1988 | European Pat. Off. |
| 0345715 | 6/1989 | European Pat. Off. |
| 0353342 | 2/1990 | European Pat. Off. |
| 0383999 | 8/1990 | European Pat. Off. |
| 0406617 | 1/1991 | European Pat. Off. |
| 0408803 | 1/1991 | European Pat. Off. |
| 0418201 | 3/1991 | European Pat. Off. |
| 8908738 | 9/1989 | WIPO |
| 9102791 | 3/1991 | WIPO |
| 9102839 | 3/1991 | WIPO |
| 9102840 | 3/1991 | |

OTHER PUBLICATIONS

Pedersen, et al., "Bleach Boosting of Kraft Pulp Using Alkaline Hemicellulases," International Pulp Bleaching Conference, vol. 2 Jun. 11–14, 1991.
Sherker, et al. "Chlorine-Free Bleaching with Cartazyme ™ HS Treatment," International Bleaching Conference, Jun. 11–19–1991, Stockholm.
Grabski, et al. "Production, Purification, and Characterization of B-(1-4)-Endoxylanase of *Streptomyces roseiscleroticus*," Applied and Environmental Microbiology, Apr. 191, pp. 987–992.

*Primary Examiner*—David M. Naff
*Assistant Examiner*—Michael V. Meller
*Attorney, Agent, or Firm*—M. Howard Silverstein; John D. Fado; Janet I. Stockhausen

[57] ABSTRACT

A method of removing color from wood pulp is disclosed. The method comprises the steps of preparing a wood pulp, treating the wood pulp with the xylanase wherein the xylanase is capable of releasing chromophores from the pulp and extracting the wood pulp to remove chromophores. In a preferred form of the invention, the wood pulp is a kraft pulp and the xylanase is selected from the group consisting of xyl 1, xyl 2, xyl 3 and xyl 4. These xylanases are obtained from *Streptomyces roseiscleroticus* NRRL-11019.

1 Claim, 24 Drawing Sheets

XYLANASE FROM STREPTOMYCES ROSEISCLEROTICUS NRRL-11019 FOR REMOVING COLOR FROM KRAFT WOOD PULPS

FIELD OF THE INVENTION

This invention generally relates to the removal of color from kraft wood pulps. Specifically, the invention relates to the use of a xylanase capable of removing chromophores in processing kraft pulps.

BACKGROUND

The cell wall of wood fiber consists of several layers composed primarily of cellulose, hemicellulose and lignin. Pulping is a procedure that disintegrates these fibers by mechanical and chemical means. Ultimately this pulp will be used for papermaking. The objective of pulping is to separate the cellulose fibers and remove as much lignin and hemicellulose as required by the end use but to preserve the fiber strength.

Kraft pulping is a specific pulping process that uses a wide variety of wood sources to produce quality pulps for the manufacture of particularly strong paper. Kraft pulping is a highly alkaline method of wood chip digestion characterized by the use of sodium hydroxide and sodium sulfide in the delignification phase. The kraft process is now the most widely used of all pulping processes. Kraft pulp is commonly used for the production of grocery bag stock and linerboard for corrugated containers and is also incorporated with other pulps into numerous grades of paper, particularly book papers, newsprint, high grade magazine paper, other printing papers, bond and writing papers.

Colored compounds ("chromophores") are created during the kraft cooking process. Chromophores are believed to be derived from either the lignin or hemicellulose components of the fiber, but the chemistry and origin of chromophores are not well characterized. The bulk of chromophores diffuse out of the pulp and are removed in the spent black liquors or in the washing stages of the kraft pulping. However, some chromophores remain in the pulp where they are either physically trapped within the fibers by precipitated xylan or are chemically bound to the hemicellulosic and cellulosic moieties.

Therefore, kraft pulp has a brown color which must be removed before the pulp can be incorporated into writing papers or printing stock. The bleaching process commonly uses elemental chlorine, chlorine dioxide, or hypochlorous acid in aqueous solution. Unfortunately, chlorination results in the formation of large quantities of chlorinated aromatic degradation products that are toxic and difficult to remove by conventional waste treatment. Moreover, the bleaching process damages the pulp fibers by reducing the degree of polymerization of the cellulose, and residual acid left in the paper causes slow degradation over time. Newer bleaching processes employ hydrogen peroxide or, less commonly, oxygen/alkali ($O_2NaOH$), but the bleaching activity of these chemicals is not great enough, particularly for high-yield pulps.

Enzymes are now commonly used to aid the pulping process. In recent years, there have been several reports that xylanases, enzymes that convert xylan to constituent sugars, will improve fiber flexibility in chemical pulps (Mora, et al. 1986, *J. Wood Chem. Technol.*, 6:147–165; Noé, et al. 1986, *J. Wood Chem. Technol.*, 6:167–184). Xylanases are known to remove residual xylan in the production of dissolving pulps (Paice, et al. 1984, *J. Wood Chem. Technol.*, 4:187–198), and to enhance the bleaching of kraft pulps (Viikari, et al. pages 67–69, in: *Biotechnology in the Pulp and Paper Industry*, Stockholm, 1986; Viikari, et al., pages 151–154, in: *Fourth International Symposium on Wood and Pulping Chemistry*, Paris, 1987; Chauvet, et al., pages 325–327, in: *Fourth International Symposium on Wood and Pulping Chemistry*, Paris, 1987). Chauvet, et al., supra 1987, reported that treating kraft pulps with xylanases lowered the lignin content of the pulps and lowered the amount of chemicals necessary for achieving a given degree of brightness. The mechanical strength properties of the sheets were not severely affected. Viikari, et al., supra 1987, has reported reductions of 25–50% in the amount of chlorine dioxide required for bleaching following treatment of kraft pulps with specific xylanases.

Many different microbial xylanase preparations have been reported in the literature. Most are derived from various fungal sources; a few are from Streptomyces and yeasts. See published PCT applications WO 91/02840, WO 91/02839, U.S. Pat. No. 4,966,850 and published European application 0 383 999.

In general, the xylanases that are most useful for facilitating the bleaching of kraft pulps are preparations that are free of cellulase activity. Enzymes that are active at neutral or alkaline pH would also be useful because large pH shifts would not be necessary in order to change the pulp from its alkaline state following the cook. Successive enzyme and alkali extraction steps would then be feasible. Temperature stability is also desirable because higher temperatures speed up enzyme activity and facilitate diffusion of the chromophores out of the pulp. The enzymes should be resistant to inhibition by the kraft degradation products. Enzymes that are capable of penetrating the micropore structure of the fibers would be very useful, because they would have access to a larger fraction of the chromophores. An enzyme that will cleave specifically at or near xylan moieties that are crosslinked into chromophores would be particularly useful, because color removal would be maximized while minimizing yield loss. Other than the present invention, there are no xylanases known to remove chromophores from wood pulp.

SUMMARY OF THE INVENTION

The present invention is a method of removing chromophores from wood pulp. The method comprises the steps of first preparing a wood pulp, treating the wood pulp with xylanase (wherein the xylanase is capable of releasing chromophores from the pulp) and then extracting the pulp to remove chromophores. In a particularly preferred embodiment of the present invention, the wood pulp is a kraft pulp and the xylanase is selected from the group consisting of xyl 1, xyl 2, xyl 3, and xyl 4. In another preferred embodiment of the present invention, the extraction is an alkali/hydrogen peroxide extraction.

The present invention is also a method of removing color from a wood pulp wherein the wood pulp contains secondary fiber. This method contains the steps of preparing a wood pulp, treating the wood pulp with xylanase (wherein the xylanase is capable of releasing chromophores from the pulp) and extracting the pulp to remove chromophores.

The present invention is also a method of removing chromophores from wood pulp containing the steps of preparing a wood pulp, treating the wood pulp with xylanase, wherein the xylanase is capable of releasing chromophores from the pulp. Chromophores are released from the pulp and the pulp is then extracted with an alkaline solution. The pulp is then subjected to bleaching. In a particularly advantageous embodiment of the present invention the xylanase is selected from a group consisting of xyl 1, xyl 2, xyl 3 and xyl 4 and the bleaching is oxygen bleaching.

The present invention is also a method of removing color from wood pulps. The method begins with the screening of xylanases to obtain a xylanase capable of releasing chromophores from wood pulp. Wood pulp is prepared and treated with the xylanase. The pulp is then extracted to remove the chromophores.

The object of the present invention is to remove color from wood pulps.

Another object of the present invention is to reduce the amount of bleaching necessary in the processing of wood pulps.

Another object of the present invention is to remove color from secondary fiber wood pulps.

An advantage of the present invention is that color may be removed from wood pulps without the use of bleach.

Another advantage of the invention is that the amount of chemical bleach used to remove color from a wood pulp may be reduced.

Other objects, advantages and features of the present invention will become apparent from the following specification when taken in conjunction with the accompanying drawings.

DESCRIPTION OF THE PREFERRED EMBODIMENT

A. In General

The present invention is a method of removing color from wood pulps. The method uses a xylanase capable of removing chromophores. We have isolated four S. roseiscleroticus xylanases that are capable of removing chromophores. Other xylanases might be equally suitable.

The following section describes the xylanases suitable for use in the present invention, xyl 1, xyl 2, xyl 3 and xyl 4. A preferred assay for the xylanases and chromophore removal and a preferred method of treating wood pulp with the enzymes is also described.

B. Characterization of the xylanases

We have isolated four endoxylanases from Streptomyces roseiscleroticus. These new xylanases are capable of diffusing into the micropore structure of the wood pulp where they bind to and hydrolyze the xylan, thereby releasing the colored materials and increasing the accessibility of the pulp to bleaching and extractive processes. The enzymes range in molecular weight from about 21–48 kDa, but they are capable of penetrating pores that are much smaller than indicated by their actual sizes. In addition, the xylanases appear to have a particular affinity for chromophores in the pulp. The S. roseiscleroticus xylanases can greatly reduce the chemical demand in chemical bleaching.

Four xylanases from S. roseiscleroticus have been purified to homogeneity. A preferential method for the purification of these xylanases is described in the Examples. The enzymes may be purified with other protein purification methods known in the art. Additionally, we envision that xylanases may be purified via a method in which genes encoding the enzyme are cloned and expressed in suitable hosts.

Figure 1:
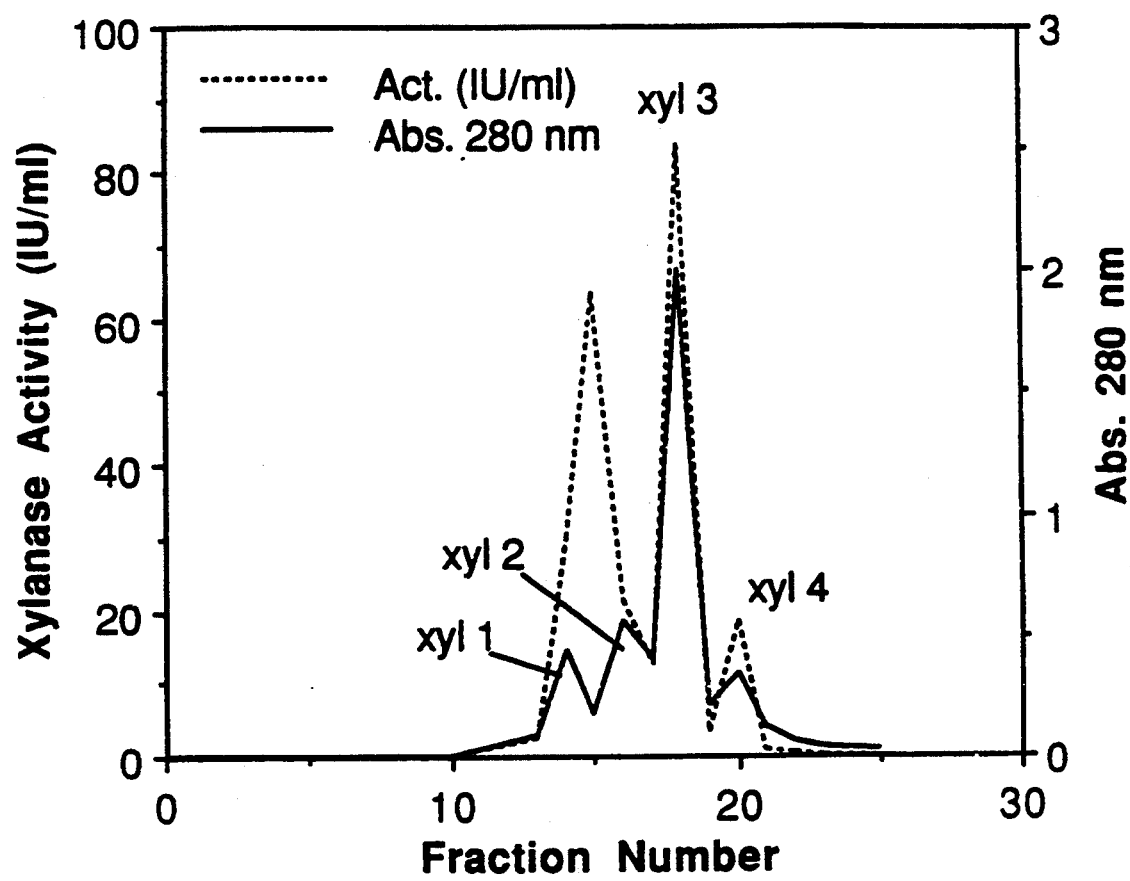
FIG. 1 is a chromatogram of both xylanase activity and absorbance at 280 nm of fractions from an SP 5PW column.
Figure 2:
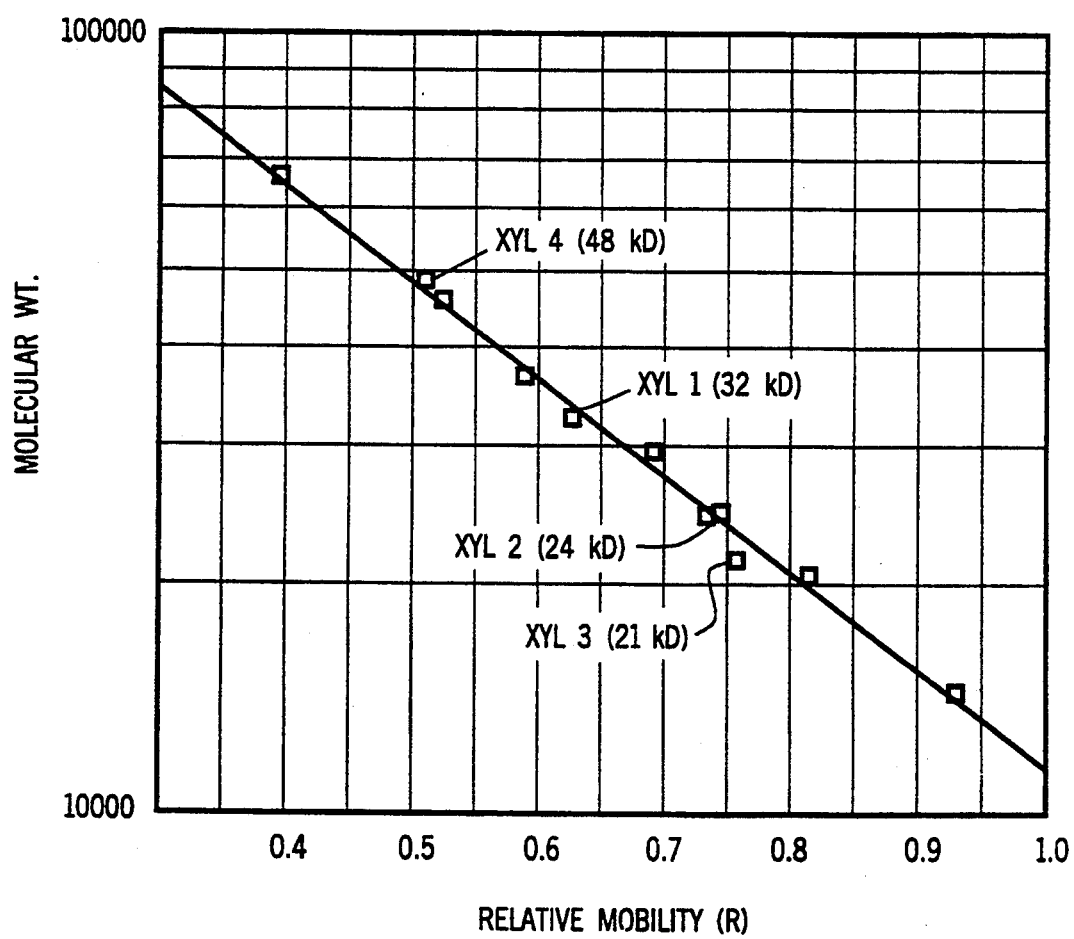
FIG. 2 is a diagram of molecular weight determination from an SDS gel electrophoretic analysis of the four xylanases.
Figure 3:
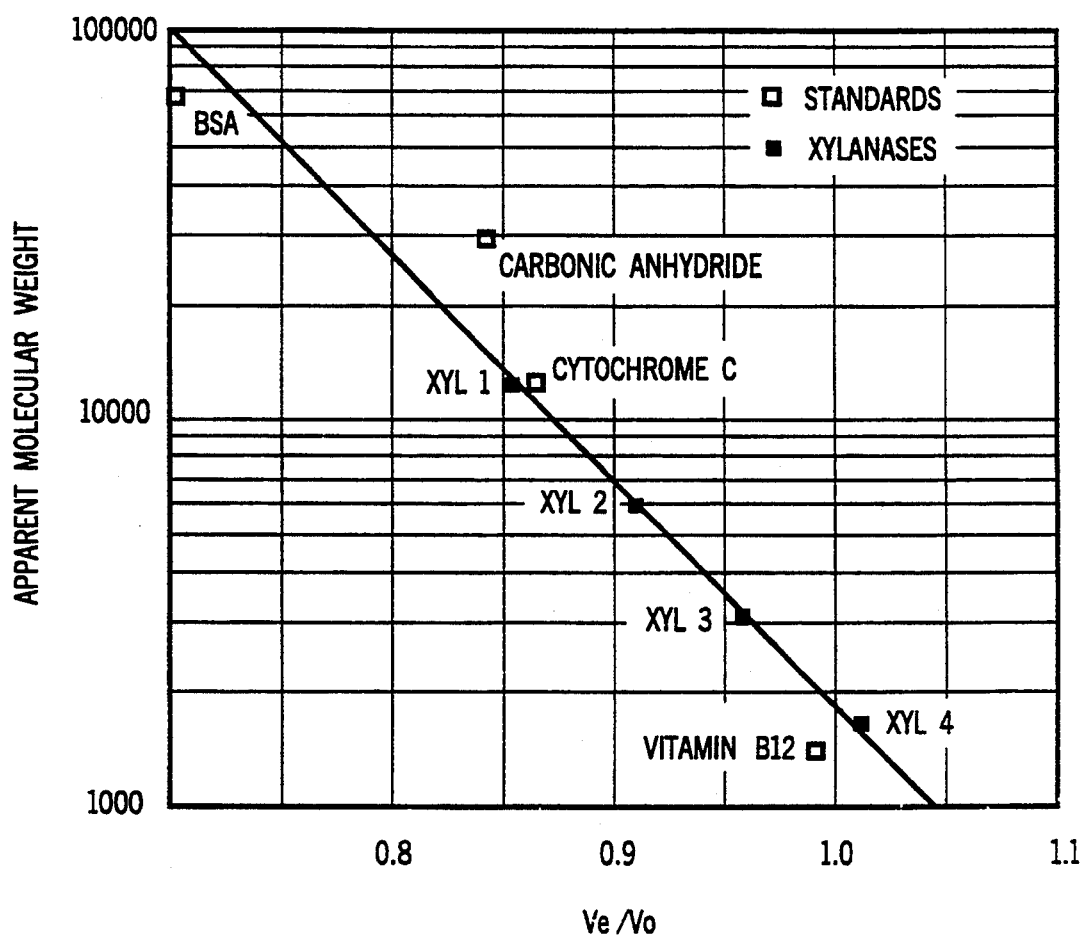
FIG. 3 is a molecular weight determination by native gel filtration on TSK.

We refer to these four isoenzymes as xyl 1, xyl 2, xyl 3 and xyl 4, according to their order of elution from a SP 5PW column (see FIG. 1). The molecular weights of the four xylanases have been estimated by both native gel exclusion chromatography using an HPLC/TSK column and by SDS (denaturing) gel electrophoresis. The apparent molecular weights determined by these two methods differ. The molecular weights estimated by denaturing gel electrophoresis, a method that is known to give a more accurate representation of true molecular weight of a protein, were between 21,000 Da and 48,000 Da (FIG. 2). By native size exclusion chromatography, the enzymes all appear to have very low molecular weights ranging from a little less than 2,000 to a little more than 10,000 Da. (FIG. 3). The molecular weight of all four xylanases have also been estimated by mass spectrometry, a method known to be extremely accurate, and found to be between 21,070 Da and 46,855 Da.

Figure 4:
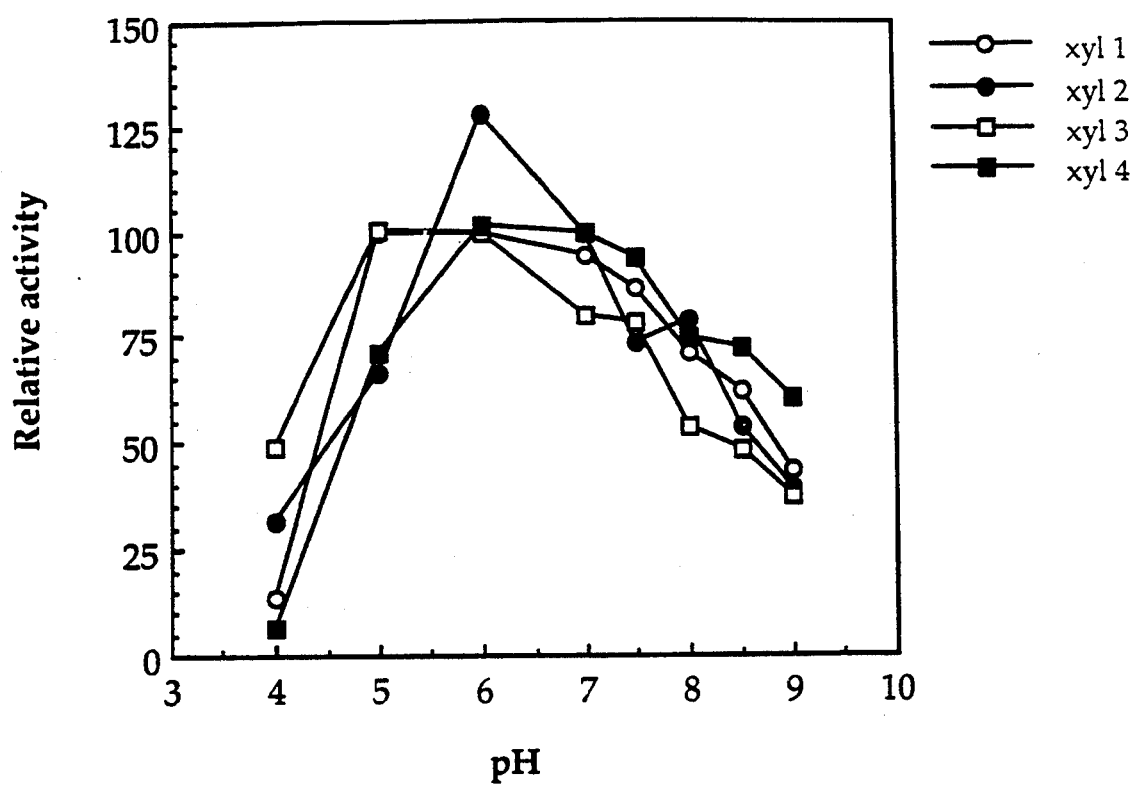
FIG. 4 is a graph of xylanase activity versus pH for four purified enzymes from Streptomyces roseiscleroticus.

The pH optima of the purified enzymes have been determined and found to lie in the range of 5 to 7, but a substantial amount of activity remains at pH 8 to 9 (FIG. 4). The pH optima of the crude preparation is not significantly different, but the crude enzyme preparation is somewhat more stable. The pH range of 7 to 8 is appropriate for removal of chromophores from kraft pulps.

Figure 5A:
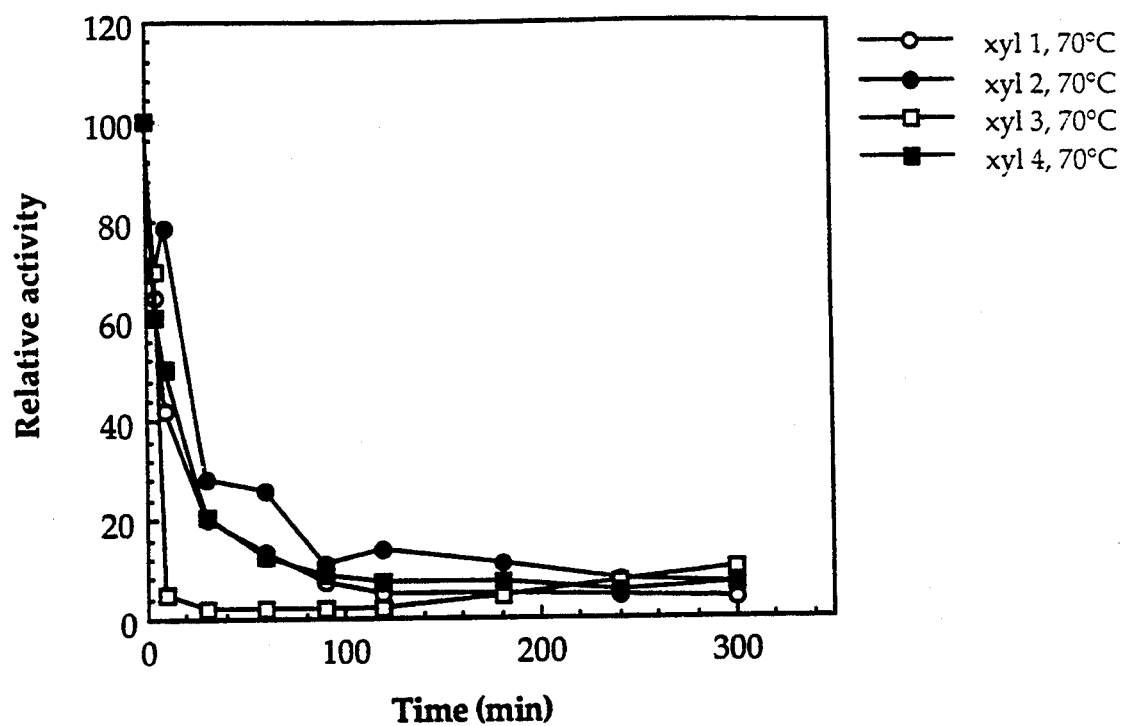
FIG. 5 is a graph of relative enzymatic activity versus time for the xylanases incubated at different temperatures.
Figure 5B:
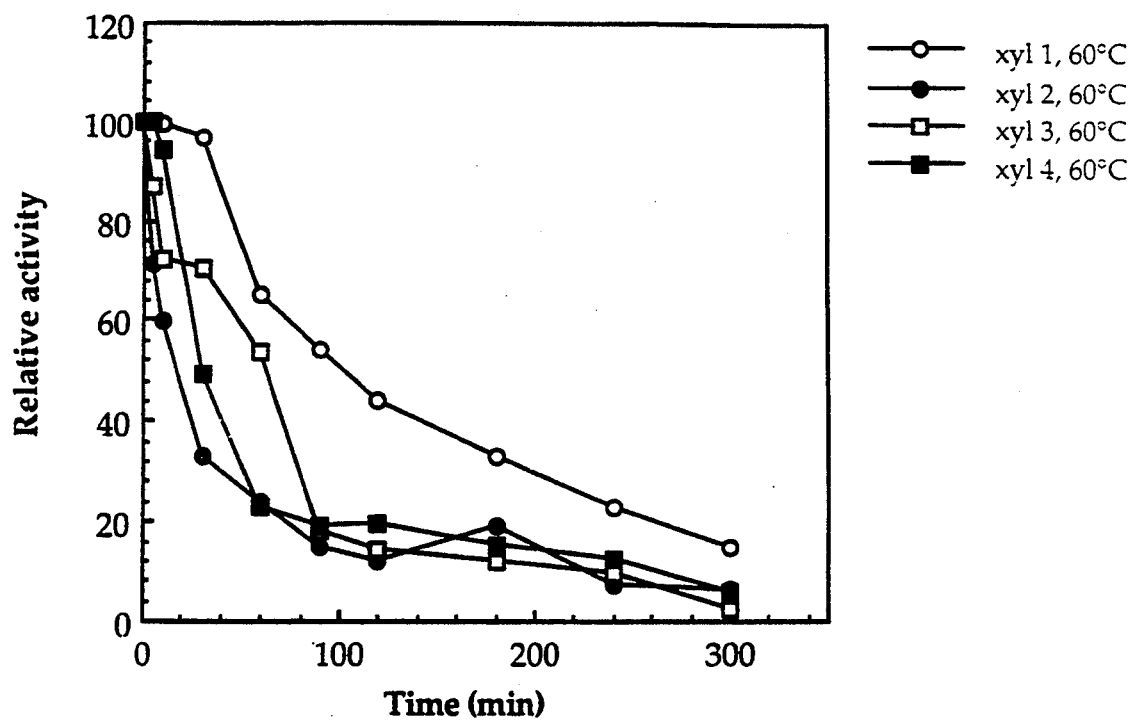
Figure 5C:
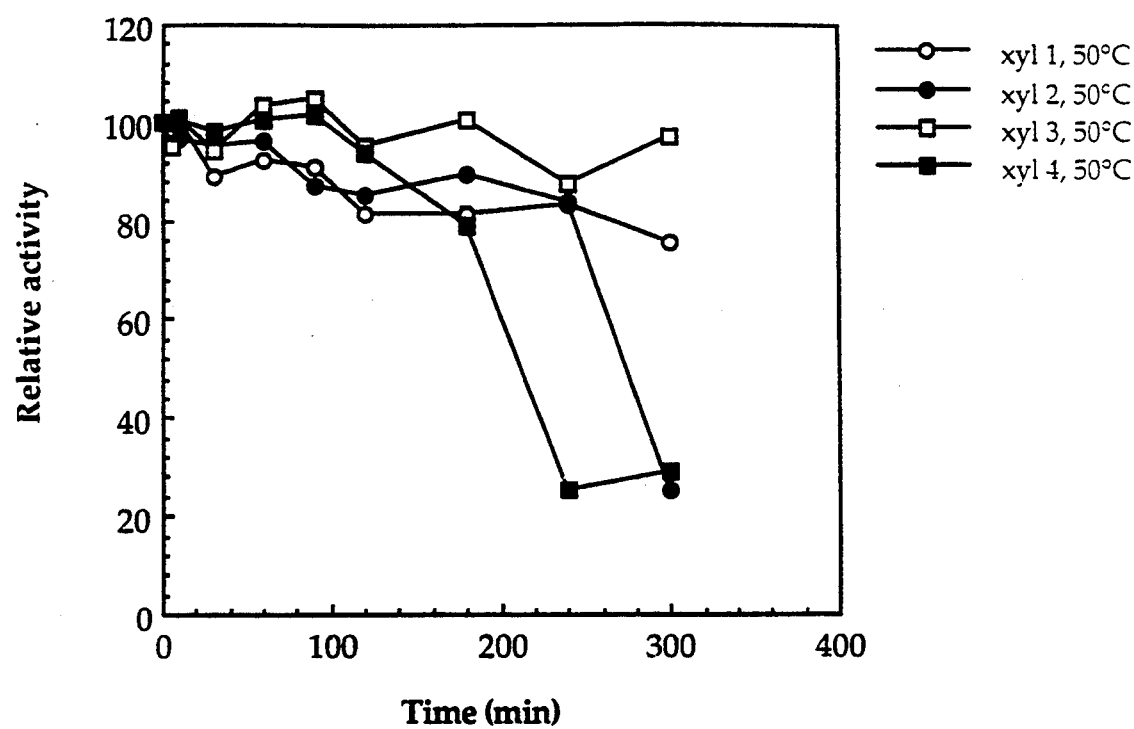

The thermal stability of the four xylanases have been determined at 50°, 60° and 70° C. At 70° C., activity is lost relatively readily, at 60° C., xyl 1 has a half-life of about 100 min; xyl 3 has a half-life of about 60 min (FIG. 5). Total xylanase activity is more stable in the crude (mixed) preparation.

All four of the xylanases exhibit an endo-action pattern, producing only xylo-oligosaccharides from oat spelts xylan. The smallest oligosaccharide observed is xylobiose. The enzymes appear to accumulate higher DP oligosaccharides (DP 10 to 18).

In comparison to many other microbial xylanases having pH optima in the range of pH 4.5 and temperature stabilities less than 40° C., the thermal stability (60° C.) and the activity of the *S. roseiscleroticus* xylanases at an alkaline pH (7 to 9) enable them to be used under conditions where the colored materials are more readily solubilized. Moreover, the relative specificity of the enzymes for chromophores minimizes pulp yield losses. Although our evidence does not indicate conclusively that the xylanases of *S. roseiscleroticus* are capable of cleaving bonds between carbohydrate and lignin or chromophores, the release of color from kraft pulp is consistent with this possibility.

C. Enzyme Assay

A preferential method of xylanase assay is as follows: xylanase activity is determined as the μmoles of reducing groups produced from a model substrate (1% hot water soluble oat spelts xylan, Sigma) in a fixed amount of time (10 to 20 min) at a fixed temperature (60° C.) at a pH of 7.0 (50 mm phosphate buffer). Hot-water soluble oat spelts xylan (0.5 ml, 2%) is placed in a series of test tubes and equilibrated in a water bath. Serial two-fold dilutions of the enzyme are made in buffer, and 0.5 ml of each dilution is added to the substrate. The reaction is stopped by the addition of Nelson-Somogyi reagent C (Somogyi, *J. Biol. Chem.* 195: 19–23, 1952). The mixture is boiled for 20 minutes, and cooled in a cold water bath. Nelson-Somogyi reagent D (1.0 ml) is added to each tube, mixed and 5 ml of water is added.

The absorbance of the solution is determined at 520 nm, and the μmoles of reducing sugars formed are compared to a standard of 0 to 300 μg of xylose. Suitable controls for the assay are the enzyme alone, substrate alone, and a buffer blank. Absorbances are determined against the buffer blank, and enzyme activities are corrected appropriately for background reducing activities. Because reaction rates are often substrate-limited, the reducing sugars observed in the two or three dilutions giving the highest consistent apparent enzyme activities are averaged. One International Unit (IU) of xylanase is defined as that amount of enzyme producing 1 μmole of reducing sugar equivalent (as xylose) in one minute under the conditions described.

D. Use of xylanases in pulping

Kraft bleaching is described in Fengel et al. *Wood: Chemistry, Ultrastructure, Reactions.* Walter de Gruyter, New York, 1984., pp. 463–473. In general, kraft bleaching comprises the following steps:

Pulp from the kraft digester is screened to remove knots, washed to remove black liquor, then screened, cleaned and thickened prior to being transferred to the brown stock holding tank or pulp chest. The pulp chest serves both as a surge tank to even out the flow of pulp from the digesters and as a mixing tank to blend the different batches of pulp. The residence time of the brown stock holding tank or pulp chest can vary from 30 minutes to 3 hours or more, depending on the timing of mill operations. Chromophore removal is usually carried out in multi-stage procedures with oxidative processes followed by alkaline extraction.

From the holding tank, the pulp passes to the bleach plant. In the first stage of bleaching, the pulp is adjusted to pH 2 either with HCl or by the addition of chlorine gas. (Note: some pH adjustment might be needed if the pulp is not fully washed or if chlorination is preceded by a strong alkali treatment). Chlorine gas dissolved in water is added with mixing.

The dose of chlorine employed depends upon the kappa number of the pulp. Kappa is determined analytically by measuring the amount of a potassium permanganate consumed by the pulp under defined conditions as given in TAPPI Standard Method 236 CM 85. Kappa number is the volume in milliliters of 0.1 normal potassium permanganate solution consumed by 1 g of OD (oven dry) pulp. The amount of chlorine added (given as % $Cl_2$ by weight based on the amount of pulp, i.e. grams chlorine/100 grams of oven dry pulp) is generally equal to $0.45 \times$ kappa. Generally one-half of the total chlorine demand is added in the first charge. The chlorine reacts with the pulp for 60 minutes at room temperature or 20 minutes at 40° C.

Following chlorination, the pulp is extracted with NaOH. The amount of NaOH employed, likewise depends on the kappa number, but generally the amount used is $0.6 \times$ the % $Cl_2$ used in the first chlorination stage. Subsequent oxidation stages can employ a mixture of $Cl_2$ and $ClO_2$ (chlorine dioxide) or simply chlorine dioxide in later stages. Generally, a 5–10% substitution of $ClO_2$ for $Cl_2$ is used but higher substitutions of $ClO_2$ have been employed to reduce the formation of chlorinated aromatics. (Note: the concentration of chlorine dioxide solutions is determined by titrating the amount of active chlorine present, so direct substitution of $ClO_2$ for $Cl_2$ is possible.) The amount of chlorine dioxide or the degree of substitution needs to be determined for the pulp employed.

A preferable method of treating a wood pulp with a xylanase capable of releasing chromophores is as follows: Xylanase is applied to the pulp after it emerges from the stock washers but before the pulp enters the bleaching process. The pulp consistency at the time of enzyme application can range from 6% to 18%. The preferable range is 8% to 12%. The pH of the pulp at the time of enzyme application can range from 4.5 to 9, but the preferable range is pH 7 to pH 8.5. The incubation temperature can range from 30° C. to 70° C., but is preferably in the range of 50° C. to 60° C. The amount of enzyme applied to the pulp can range from 0.05 to 5.0 units (U) per oven dry gram of pulp, but preferably is in the range of 1 to 3 U/g.

The enzyme is applied to the pulp in a dilute solution with good mixing of the pulp stock. Mixing is especially important for effective treatment at low dosing levels. The enzyme/pulp mixture is held for 0.5 to 3 h, but preferably for 1 to 2 h, during which time enzyme action takes place and chromophores are released. Following enzyme treatment, the pulp is filtered and washed to remove these chromophores and residual enzyme. If desired, the enzyme-treated pulp can be extracted with alkali or alkali plus hydrogen peroxide in order to remove lignin prior to the bleaching stage. The enzyme-treated pulp is then bleached following any one of several bleach processes or sequences.

E. Assay for release of chromophores

Release of chromophores is routinely assayed by measuring the optical density of the supernatant solutions after enzyme treatment or alkali extraction. Complete spectra may be obtained from 200 to 400 nm, or the absorption may be measured at 237 nm. Absorption in the visible region (400 to 700 nm) is usually minimal and results in a flat spectrum. Alkali-extracted materials often absorb strongly in the region between 260 and 280 nm.

F. Other xylanases capable of releasing chromophores

The exact number of species that produce xylanases is not known. Xylanases are commonly made by fungi, Streptomyces and by other Actinomycetales. To obtain other xylanases capable of releasing chromophores, one would first identify and purify a xylanase. The xylanase may be a naturally occurring xylanase or may be obtained from a cloned gene. The enzyme would then be used to treat a wood pulp, preferably as described above. The pulp could then be analyzed, as described above, to determine whether chromophores had been released.

We have developed a systematic process for isolating and screening novel microbes for their abilities to release chromophores. The rationale for our isolation and screening process is the following: Organisms that are most useful would be expected to grow on the residual materials left after wood or pulp decay. Streptomyces, a genus known to produce xylanases, are normally soil-inhabiting organisms, and species capable of removing chromophores composed of lignin or hemicellulose degradation products should be found growing on extensively rotted wood or leaf litter. Streptomyces are also known to grow favorably under neutral to alkaline conditions. Useful isolates could also be found in soils, mud or aqueous systems receiving or in the vicinity of facilities receiving effluent from kraft pulp or bleach plants.

One suitable method of obtaining novel isolates is the following: An extract or infusion of rotted pine, birch, compost or leaf litter is made by crumbling or shredding the material and placing it in a large beaker. The material is covered with water and allowed to simmer for 15 to 60 minutes. The liquid is removed by filtration through several layers of cheesecloth and sterilized by autoclaving. Rotted birch wood is preferred for its high hemicellulose content.

Approximately 300 ml of the infusion is diluted with 700 ml of water. 1.0 g of yeast extract is added along with 15 to 18 g of agar. Minerals, other trace elements and fungal inhibitors may be added if desired. (See Hunter-Cevera, J. C., et al. 1986. In: Demain, A. L. and Solomon, N. A. *Manual of Industrial Microbiology and Biotechnology*, American Society for Microbiology, Washington, D.C.). The agar is dissolved by heating, the solution is sterilized by autoclaving and poured into sterile Petri plates. After the agar solidifies, the plates are allowed to dry for several days at room temperature or for up to an hour in a sterile hood with a fan blowing and the lids cracked. Care is taken to periodically rotate the plates so that drying is even.

Soil, mud or water samples are gathered from various habitats. Neutral to alkaline soils are preferred, as are soils with high organic content. Samples may also be taken from compost piles, rotted wood, the surfaces of plants or from plant root rhizosphere. A plurality of samples are removed from multiple soil horizons or micro-habitats. The soil samples are allowed to air dry, screened to remove large particles, and ground with a mortar and pestle. The soil may then be applied to the surface of the isolation agar either by using a moistened foam sponge or by dilution and plating. Foam sponges of they type used to seal culture tubes are very suitable. The sponge is dipped into the soil, the excess soil is removed by gentle tapping, then the sponge is repeatedly pressed against the surface of the agar in a progressive circular pattern. Up to 20 impressions may be made on a single standard Petri dish. Multiple types of agar may be employed in alternating sequence. In using the dilution and plating technique, 1 g of dried, pulverized soil is diluted in 100 ml of sterile 0.85% NaCl in a 500 ml Erlenmeyer flask, and shaken at 250 rpm for 15 to 30 min. Samples are removed and carried through a series of dilutions. Samples from each of the dilutions are then spread onto the surface of the agar with a bent glass rod.

Replicate plates are incubated at 30° C., 35° C., 40° C. and periodically examined for microbial growth. Colonies exhibiting characteristic features of Actinomycetes are isolated by removing them from the plate with a sterile toothpick or a sterile needle and by streaking them for isolation on a fresh plate of the same medium from which they are isolated.

Secondary screening of the organisms consists of testing the ability of the isolate to grow on alkali-extracted, milled wood enzyme lignin (AEMWEL) as a sole carbon and energy source. AEMWEL is made by the following procedure: Pine or birch chips are soaked in 1% sodium hydroxide (oven dry wood basis) at 37° C. overnight. The alkali extract is removed by filtration; the wood chips are washed repeatedly by soaking in water and rinsing until the rinse water is less than pH 7.5. The chips are then dried and ground in a Wiley mill to pass a 40 mesh screen. The ground wood is then extracted with acetone:water (90:10). The extracted, ground wood is dried extensively in a vacuum oven to remove all residual moisture. Once dry, the wood is ball-milled for 48 h. The ball-milled wood is digested in several successive treatments with an excess mixture of cellulases and hemicellulases. Enzymes are removed by repeatedly washing the residual AEMWEL in distilled water and recovering the solids by centrifugation. The residual AEMWEL consists essentially of lignin covalently attached through alkali-stable bonds to residual carbohydrate moieties. Other methods for isolating lignin or lignin-carbohydrate compounds may be suitable. See Azuma, et al. *Methods Enzymol.* 161:12–18 (1988); Obst, et al. *Methods Enzymol.* 161:3–12 (1988).

AEMWEL is used as a sole carbon and energy source in the second round of screening. A low concentration (0.5%) of AEMWEL is suspended in distilled water plus trace elements and 0.1% to 0.55% yeast extract, 1.5 to 1.8% agar is added and dissolved and the solution is sterilized by autoclaving as previously. Small aliquots (~1.0 ml each) are placed in each well of 24-well plates and allowed to solidify. Each isolate is inoculated into a single well of the plate, and the plates are incubated at a suitable temperature (30° to 45° C.). After 5 to 20 days, the plates are examined and the isolates are scored for growth. Isolates capable of growing on AEMWEL are subjected to a third screen consisting of an ability to produce clearing zones in agar plates containing 0.5 to 2% oat spelts xylan or glucomannan as the sole carbon and energy source.

Isolates showing relatively good growth on AEMWEL and glucomannan and large clearing zones on xylan are screened for their ability to release color from kraft pulp. In this screening procedure, isolates are cultivated as described for *Streptomyces roseiscleroticus*, and the supernatant solution is assayed for enzyme production. The obtained enzymes are assayed as above for their ability to release chromophores.

Isolates may also be obtained from culture collections and screened in this manner. Cultures may be grown under several different aeration rates, and the supernatant solutions are harvested and concentrated.

EXAMPLES

A. Preparation of *S. roseiscleroticus* cultures.

*Streptomyces roseiscleroticus* (NRRL B-11019) was obtained from David P. Labeda, USDA Northern Regional Research Laboratory, Peoria, Ill. The strain may be obtained commercially from Northern Regional Research Center, Peoria, Ill. The strain NRRL B-11019, a bacteria of the order Actinomycetales, was deposited with NRRL under the terms of the Budapest Treaty on Jun. 29, 1992. *S. roseiscleroticus* was cultured on a liquid xylan medium (YMX=yeast extract, 4.0 g/l; malt extract, 10.0 g/l; xylose, 4.0 g/l; agar 15 g/l; pH was adjusted to pH 7.3 prior to autoclaving) in order to achieve maximum xylanase enzyme production. It was essential to subculture the organisms frequently (every two weeks) in order to maintain viability. Stock inocula were preserved at an early stage by cutting plugs of agar from one-week old YMX agar plates and freezing at −70° C. in 10% (v/v) sterile glycerol. In order to obtain maximal xylanase production, it was necessary to prime the cultures in TSB as described by Morosoli, et al., *Biochem. J.*, 239: 587–592 (1986).

Seven-day old (or sporulating) slants grown on DX agar were washed with sterile TSB. 10 ml were used to inoculate 100 ml of TSB in a 500 ml Erlenmeyer flasks stoppered with cotton plugs. Cultures were incubated at 37° C. to 38° C. with shaking at 240 rpm for 24 hours. Primer cultures were assayed for xylanase activity, and those with the highest xylanase titers were used as inoculum. The full 110 ml inoculum was added to 500 ml of XP medium in a 2800 ml Fernbach flask (see Grabski and Jeffries, Appl. Environ. Microbiol. 57: 987–992 (1991). Cultures were incubated at 37° C. to 38° C. with shaking at 240 rpm for 48 to 72 hours. Xylanase assays were performed at 12 hour intervals, and cultures were harvested when xylanase activity peaked. Duplicate cultures were used for xylanase production.

To assay for xylanase activity, samples (1.0 ml) were taken every 24 hours and cells were removed by centrifugation (10,000×g, 15 min.). All sugar analyses were performed by the Nelson-Somogyi method (*J. Biol. Chem.* 195: 19–23, 1952) using either D-xylose or D-glucose as a standard. The 1 ml samples were centrifuged at 10,000×g for 15 min. to pellet and remove the cells. Supernatant solutions were then decanted and assayed for xylanase activity. Xylanase assays employed 0.25 ml of 1% oats spelts xylan (Sigma) plus 0.25 ml of appropriately diluted enzyme in 50 mM sodium phosphate buffer, pH 7.0. Xylan was solubilized in 0.5N NaOH and neutralized with 1.0N HCl. Reactions were started by the addition of substrate and incubated for 10 min at 60° C. Reactions were stopped by the addition of Nelson-Somogyi reagent C. Cultures were sampled and assayed on a daily or more frequent basis. Maximal titers of xylanase activity were generally attained on day 3 or 4. Cultures were harvested when maximal activity was thought to have been attained. The optimal time of harvest could be determined experimentally by leaving one or more flasks on the shaker and continuing to sample them after the time of harvest.

Cellulase activity was assayed only at peak xylanase timepoints. Cellulase assays were performed in the same manner as above except that 1% phosphoric-acid swollen (Walseth) cellulose was used as a substrate, and the assay temperature was reduced to 55° C. The ratio of xylanase to cellulase activities in the crude preparation was generally greater than 75. In the purified xylanase preparations, cellulase activity was not detected.

2. Enzyme Purification

Step (a) Clarification. Cells were harvested by centrifugation (10,000×g, 30 min). The dark red supernatant was decanted and pellets were discarded. The supernatant was treated with the minimum amount of Biocryl BPA-1000 (Rohm and Haas Co., Philadelphia, Pa.) required to precipitate pigments to approximately 20% of the initial value, as measured by reduction in absorbance at 392 nm. BPA-1000 is used as supplied by the manufacturer and typically 1.5% to 2.5% (v/v) is required for clarification. After stirring with the BPA for 5 min. at 4° C., a milky-grey floc was formed. This precipitate was removed by centrifugation at 15,000×g for 15 minutes. The clear, light yellow supernatant that remained was filtered through Miracloth (Calbiochem, La Jolla, Calif.).

Step (b) Concentration. The BPA-clarified filtrate was concentrated 5-fold by ultrafiltration in a Lab 1 EX ultra-filtration system (Rohm and Haas Co., Philadelphia, Pa.) using a 0.093 m$^2$ PM-1 hollow-fiber cartridge (1,000 mol wt cut-off) at a transmembrane pressure of 10 psi. The retentate (200 ml) was diafiltered with 250 ml of 100 mM pH 5.5 sodium acetate buffer followed by 500 ml of 10 mM pH 5.5 sodium acetate (Buffer A). Final retentate volume after diafiltration was approximately 200 ml.

The retentate was transferred to a 50 ml stirred ultrafiltration cell (Amicon Div., Grace & Co., Danvers, Mass.) equipped with a YM-3 disc membrane (3,000 mol wt cut-off) and concentrated 5-fold. The retentate was diafiltered with buffer A until a pH of 5.5 was attained. The volume was approximately 40 ml after diafiltration.

Step (c) purification. The YM-3 retentate was centrifuged at 15,000×g, 15 min. Pellets were discarded and the supernatant, 40–60 mg protein/load, was applied (6 ml/min.) to a 21.5 mm×150 mm TSK SP-5PW column. Proteins were separated using a gradient HPLC system (Beckman Instruments, Inc., Waldwick, N.J.) consisting of two 114M preparative head pumps, model 165 variable wavelength detector, and model 210A sample injection valve. The elution buffers were buffer A and buffer A+1.0M NaCl (buffer B). Unbound proteins were washed from the column with 100% buffer A/15 min. Chromatography of adsorbed proteins was achieved with a discontinuous gradient of buffer A/B as follows [%(v/v) A/min.]: 100/0, 100/5, 50/30, 0/32, 0/35, 100/37, and 100/50. Elution was monitored by absorbance at 280 nm for protein, and 6-ml fractions were collected. A chromatogram describing this elution is presented at FIG. 1. The order of elution on the SP 5PW column determined our nomenclature for the four xylanases.

Fractions containing xylanase activity against oat spelt xylan, as measured above, were pooled according to activity, protein chromatogram, and SDS-PAGE determinations of purity. The four xylanase peaks containing the highest enzyme activity and absorbance at 280 nm eluted between 300 and 400 mM NaCl. Xylanase fractions from three HPLC runs were concentrated and diafiltered into buffer A to a final protein concentration of approximately 9 mg/ml, using a stirred ultrafiltration cell as described above. $(NH_4)_2SO_4$ was added to the sample to a final concentration of 1.25M. The sample was microfuged at 16,000×g for 3 min. Pellets were discarded and the supernatant, 20–30 mg protein/load, was applied (1 ml/min.) to a 7.5 mm×75 mm TSK Phenyl-5PW column. Proteins were separated using a Beckman gradient HPLC system consisting of a 126 dual analytical pump, a model 165 variable wavelength detector, an IBM PC based data/system controller (Beckman System Gold software), and a model 210A sample injection valve. Elution buffers were buffer A and buffer A+1.25M $(NH_4)_2SO_4$ (buffer C). Unbound proteins were washed from the column with 100% buffer C/10 min. Chromatography of adsorbed proteins was achieved with a discontinuous gradient of buffer C/A as follows [%(v/v) C/min.]: 100/0, 100/5, 35/8, 0/25.5, 0/30, 100/32, and 100/45. Elution was monitored at 280 nm for protein, and 1-ml fractions were collected. The xyl 3 peak is commonly homogeneous after this step. Xyl 1, xyl 2 and xyl 4 must be further purified by gel-filtration chromatography.

Fractions were pooled according to activity, protein chromatogram, and SDS-PAGE determinations of purity as above. Pooled fractions of xyl 1, xyl 2, xyl 3 and xyl 4 from the Phenyl-5PW HPLC runs were concentrated and diafiltered into 200 mM pH 7.0 sodium phosphate (Buffer D) to a final protein concentration of approximately 5–10 mg/ml, using a Centricon-3 (Amicon Div., Grace & Co., Danvers, Mass.). The enzyme was microfuged at 16,000×g for 3 min. Pellets were discarded and the supernatant, 200–600 μg protein/load, was applied (1 ml/min.) to a 7.8 mm×150 mm TSK QC-PAK gel-filtration column. Proteins were separated using the Beckman analytical HPLC system previously described using isocratic elution with buffer D. Elution was monitored at 280 nm for protein, and 0.5 ml fractions were collected. Purified xylanases (10 mg/ml) were stored in 50 mM sodium phosphate buffer pH 7.0 at −70° C.

Protein purity and molecular weight were determined by sodium dodecyl sulphate polyacrylamide gel electrophoresis (SDSPAGE) on a Pharmacia Phast System (Piscataway, N.J.) using 10%–15% gradient polyacrylamide gels and a Sigma SDS-7 standard (Sigma Chemical Co., St. Louis, Mo.) containing seven proteins in the 14,200 to 66,000 mol wt range, staining with Coomassie Brilliant Blue G250. FIG. 2 describes the results of this analysis. The four xylanases are 21–48 kDa.

Protein concentrations were determined by the method of Lowry et al. (1951), with bovine serum albumin, Cohn fraction V (Sigma Chemical Co. St. Louis, Mo.) as standard.

3. Enzyme characterization

Protein purity and molecular weight were determined by gel-filtration chromatography using the same TSK QC-PAK column and conditions described above in the purification protocol. Sigma standards for gel-filtration and corresponding molecular weights were: blue dextran (2,000,000), bovine serum albumin (66,000), cytochrome C (12,400), and vitamin $B_{12}$ (1,400). The results are described in FIG. 3, where molecular weights range from 1,400 to 66,000 Da.

The molecular mass of all four xylanases was determined with a Finnigan MAT TSQ-700 triple sector quadrupole mass spectrometer equipped with an electrospray ion source. Samples were introduced with an on-line capillary HPLC. A standard water, acetonitrile, trifluoroacetic acid buffer system was used in the chromatography (Beavis, 1990 reference). Scans over the mass range m/z 500–2000 were taken at 5 sec. intervals during the course of the liquid chromatography run. Chromatograms were generated by monitoring the ion current to the mass spectrometer detector. Mass spectra were collected as centroid data.

The molecular weights of the four xylanases as determined by mass spectrometry were as follows:

TABLE 1

| | |
|---|---|
| xyl 1 | 33,647 Da |
| xyl 2 | 33,655 Da |
| xyl 3 | 21,070 Da |
| xyl 4 | 46,855 Da |

Thus, even though xyl 1 and xyl 4 have similar N-terminal amino acid sequences, they can be distinguished by their molecular masses. Even though xyl 1 and xyl 2 have similar molecular masses, they can be distinguished by their amino acid sequences.

Figure 6:
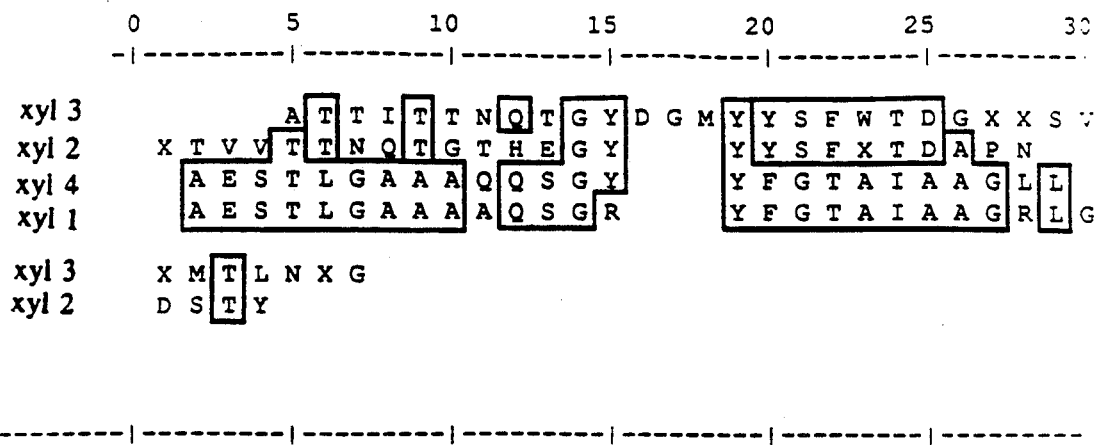
FIG. 6 is the N-terminal amino acid sequences of xyl 1, xyl 2, xyl 3 and xyl 4.
Figure 11:
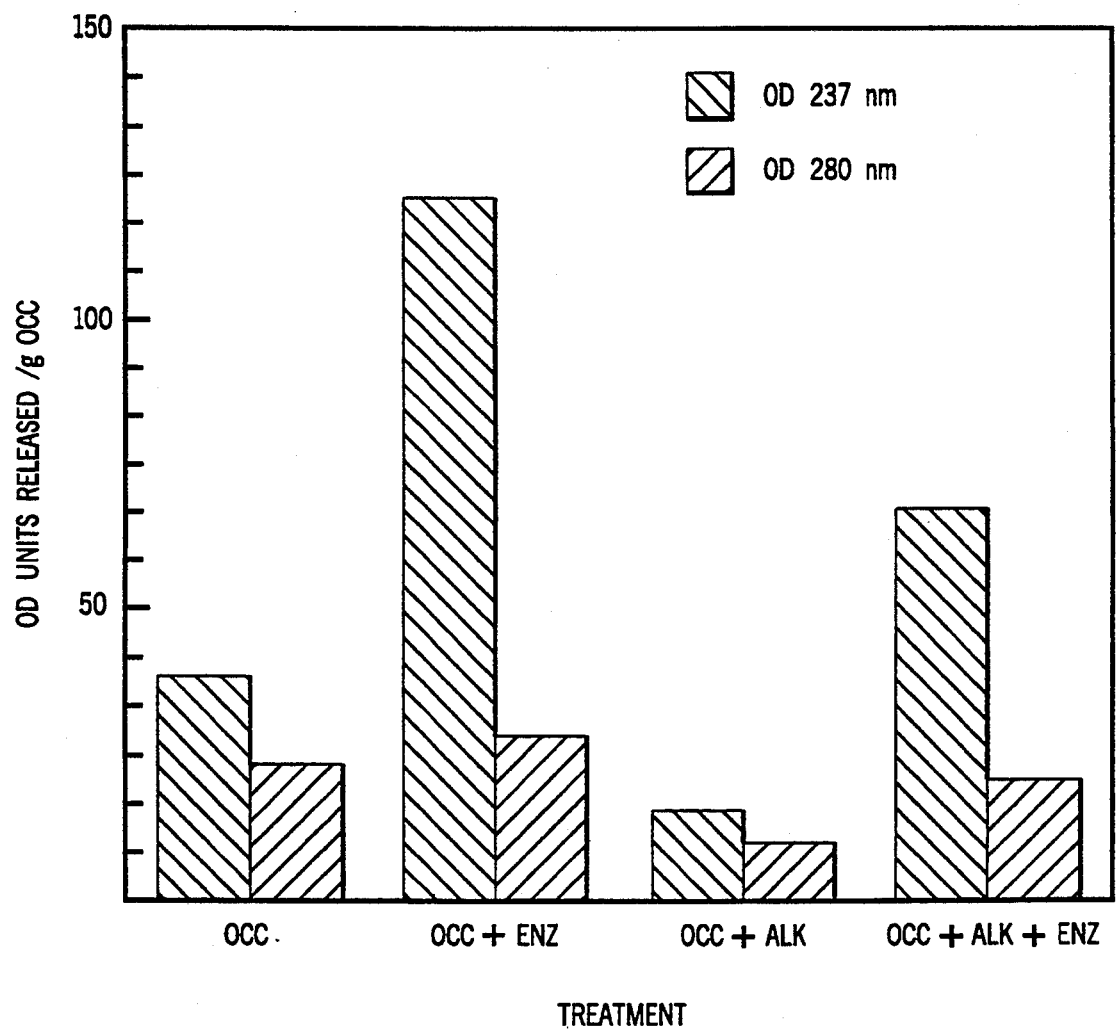
FIG. 11 is a diagram comparing release of chromophores versus different treatments involving old corrugated containers (secondary fibers).

N-terminal sequences were determined by gas phase sequencing on Applied Biosystems (Foster City, Calif.) model 475A protein sequencer at the University of Wisconsin Biotechnology Center using the protocols, reagents, and solvents supplied by the manufacturer. The N-terminal amino acid sequences of all four of the enzymes were determined and are described in FIG. 6 and at SEQ ID NOs: 1–4. Where the amino acid could not be identified, an X is shown. The sequences are lined up to maximize homology. Single letter designations stand for the various amino acids. Residues are boxed in FIG. 11 to indicate homology. Referring to FIG. 11, two of the xylanases (xyl 1 and xyl 4) had some similarity of their N-terminal amino acid sequences (88% homology). The other two xylanases (xyl 2 and xyl 3) showed about 37% homology. All four enzymes possess some common amino acid sequences.

With regard to N-terminal amino acid sequence, xyl 3 appears to be similar to other low molecular weight xylanases described from Streptomyces (published PCT application WO 91/02791; published European application 0 353 342). However, the molecular weight of xyl 3 differs from that reported for the xylanase described in 0 353 342 (5,000 Da) and WO 91/02791 (25,000 Da). Additionally, there are amino acid sequence differences between the xyl 3 sequence and the N-terminal amino acid sequences from the two reported xylanases. The amino acid sequences of xyl 1, xyl 2 and xyl 4 are novel.

4. Treatment of Pulp a. In General

The clarified, concentrated, and diafiltered xylanase enzyme preparation was then diluted and applied to kraft pulp at the desired concentration. In general, the treated pulp is incubated with the enzyme, washed, extracted with NaOH, and bleached with an amount of bleach determined from the kappa of the enzyme-treated pulp. We found that the xylanase-treated pulp has a lower kappa and, therefore, requires less bleach than the control pulp in order to achieve the same brightness in both samples. The following examples illustrate the treatment of kraft pulps with the *S. roseisclerotius* xylanases.

b. Kappa reduction of kraft pulp by *S. roseisoleroticus* xylanases

The kraft pulp consisted of mixed northeastern U.S. hardwoods (chiefly aspen). The starting material consisted of 18.3% solids. The initial kappa number of the pulp was 16.3. 150 g OD was thoroughly washed prior to use. The starting pH was 7.8, and the final wet wt was 820 g. The titer for the xylanase mixture was 35 IU xylanase/ml. The buffer consisted of 150 ml of 50 mM phosphate, pH 7.0. The balance of the reaction mixture was water. Enzyme loading rates were 13.13 or 5 IU/g OD pulp.

Duplicate samples of pulp (820 g wet) in a plastic bag, buffer (150 ml), and water (530 ml for enzyme treatment; 550 ml for control) were each equilibrated separately at 60° C. The enzyme was kept on ice until just before the pulp treatment was initiated. Treatment was started by diluting the enzyme in the pre-equilibrated buffer and water, and adding the enzyme solution to the pre-equilibrated pulp with simultaneous mixing. Controls were performed in a similar manner but with water substituted for enzyme. The pulps were periodically mixed by kneading the bags during 3 hours of incubation at 60° C. Following incubation, the pulps were dewatered on a Buchner filter, washed and preheated to 65° C. prior to the addition of 1.5 g NaOH per 150 g OD pulp (1% NaOH by wt, 5% consistency). The pulps were extracted for 1 hour at 65° C., dewatered by filtration on a Buchner funnel and washed repeatedly with 60° C. water until the wash waters were neutral.

The kappa content of the pulp was reduced by the enzyme treatment as shown in the following table:

TABLE 2

| sample | Enzyme treatment | kappa number |
|---|---|---|
| Starting pulp | none | 16.3 |
| Control | none | 16.0 (after extraction) |
| Sample | 5 IU/g OD | 13.04 (after extraction) |

Therefore, enzyme treatment reduced the kappa number by 18.5% in comparison to the control. The chlorine demand should be reduced by an equivalent amount.

c. Xylanase enhancement of oxygen bleaching of a hardwood kraft pulp 150 g OD of eastern hardwood pulp was treated as according to the procedure in Example 4(b). Following enzyme treatment and alkali extraction, the pulps were bleached with an elemental chlorine-free bleaching sequence that employed sodium hydroxide (2.25% on an OD basis) plus hydrogen peroxide and 1.1% chlorine dioxide ($ClO_2$).

Results were as follows:

TABLE 3

| Sample | Enzyme treatment | kappa number | Viscosity (cps) | Final brightness |
|---|---|---|---|---|
| Starting pulp (hardwood) | none | 17.0 | ND | ND |
| Control (following bleaching) | none | 16.1 | 56.0 | 76.9 |
| Enzyme-treated (following bleaching) | 5 IU/g OD | 14.5 | 56.4 | 81 |

Enzyme treatment therefore increased brightness and viscosity while reducing kappa.

d. Xylanase enhancement of a chlorine bleach sequence for southern pine kraft pulp In this example, the material consisted of 150 g OD of southern pine kraft pulp treated as in Example 4(b) above. The resulting sample and control pulps were subjected to a 50% reduced $Cl_2$ bleaching sequence (i.e., only half of the standard amount of elemental chlorine was employed). The bleach sequence employed was as follows: CEHED where C is elemental chlorine ($Cl_2$); E is alkali (1%); H is hydrogen peroxide (0.5%) and D is chlorine dioxide ($ClO_2$). Brightness can be measured by several standards and test methods including Tappi Standard T 217M-48, T 218 OS-75, SCAN-C 11:75 or ISO 3688-1977 E). The most commonly used brightness value represents the reflectance value of blue light at 375 or 360 nm of a pulp sheet (in %) based on the reflectance of magnesium oxide as a standard sample. ISO brightness values were used unless otherwise stated.

The results were as follows:

TABLE 4

| Sample | kappa number | Bleached Brightness |
|---|---|---|
| Initial pine kraft pulp | 25.9 | ND |
| Control pine kraft pulp following alkali extraction | 22.56 | ND |
| Enzyme-treated pine kraft pulp following alkali extraction | 22.12 | ND |
| Control following bleaching (duplicate samples) | ND | 76.0 |
|  | | 76.0 |
| Enzyme-treated following bleaching (duplicate samples) | ND | 79.9 |
|  | | 79.9 |

Therefore, the brightness of the pulp was enhanced with enzyme treatment. In the same manner, We also obtained an enhanced bleaching effect for eucalyptus pulp.

e. Enhancement of chlorine bleaching by enzyme treatment, alkali and hydrogen peroxide extraction Softwood (pine) kraft pulp with an initial kappa of 29, a brightness of 32 and a viscosity of 20 was treated with 5 IU/g OD of a mixture of the four xylanases and subsequently extracted with either alkali (1%, OD pulp basis)

or alkali plus hydrogen peroxide (0.5%, OD pulp basis). Control pulps were extracted with either alkali or alkali plus peroxide as in the test condition, but were otherwise unaltered. Following enzyme and alkali or alkali plus peroxide treatments, pulps were bleached with chlorine using 10% chlorine dioxide substitution (CD) at one of four levels. The total amount of active chlorine used was equal to the lignin content as determined by micro kappa (k) multiplied by 0.18, 0.14, 0.10 or 0.06. The amount of sodium hydroxide employed in the E1 was equal to the active chlorine multiplied by 0.55. Similar calculations were employed in the D1 and D2 stage treatments with chlorine dioxide. E1p and E2p extractions used 1% NaOH plus 0.5% $H_2O_2$.

Figure 7:
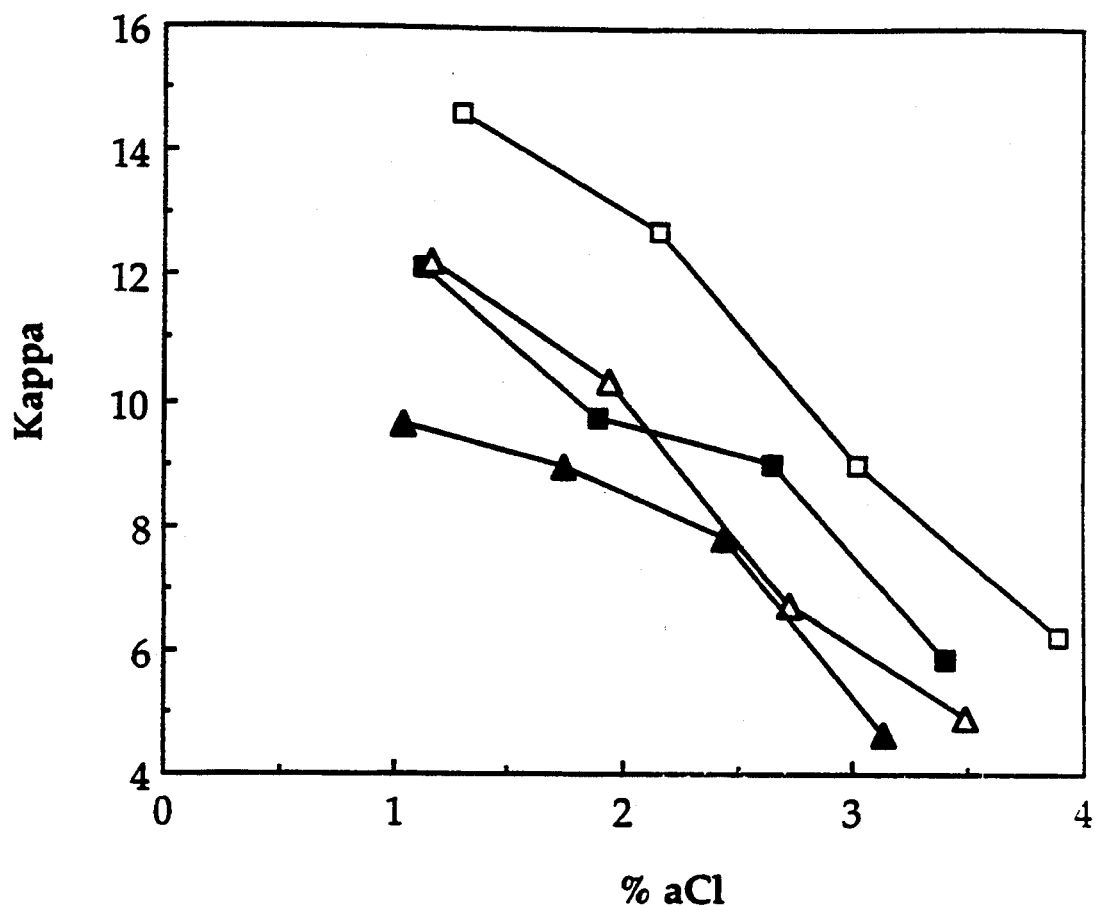
FIG. 7 is a graph of the effect of alkali, xylanases, and hydrogen peroxide on the chlorine requirement for bleaching a softwood kraft pulp.
Figure 8:
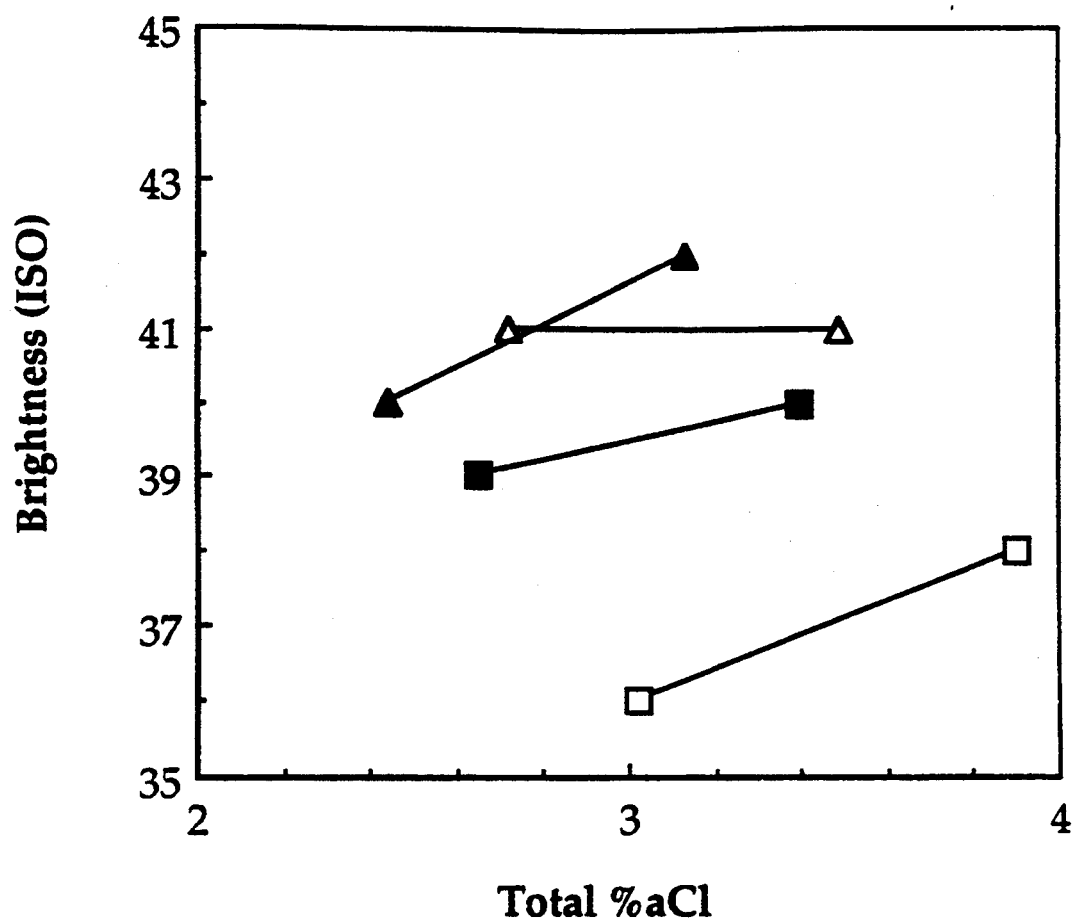
FIG. 8 is a diagram of the effects of the xylanases, alkaline extraction and hydrogen peroxide on the brightness of the softwood kraft pulp.

The results are reported graphically in the following FIGS. 7 and 8. It can be seen that enzyme treatment reduced the amount of chlorine required to attain a target kappa of 7 by about 30%. Hydrogen peroxide also reduced the amount of chlorine required, and the combination of enzyme with peroxide was particularly effective at low levels of aCl.

5. Chromophore removal

Figure 9:
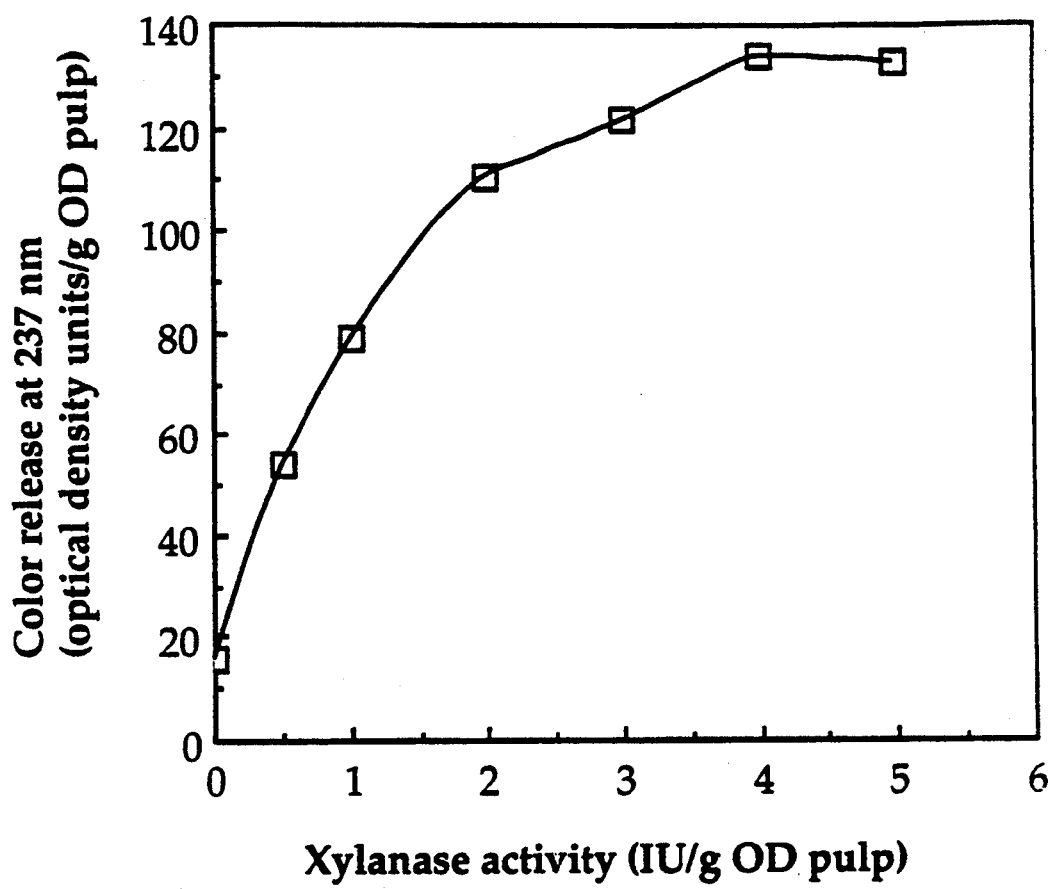
FIG. 9 is a diagram of chromophore release, as measured by absorbance at 237 nm, versus xylanase concentration.

Beyond the ability to reduce the kappa number and enhance bleaching, however, the xylanases actually remove color from the pulp (FIG. 9). This is a characteristic not observed with other xylanases known to enhance bleaching. A southern red oak kraft pulp was treated with crude xylanase from *S. roseiscleroticus* at various enzyme levels, and the amount of color removed was determined spectrophotometrically at 237 nm. The pulp was treated with enzyme as per Example 4(b) except that 10 mM phosphate buffer, pH 7.0 was employed, and enzyme dosing levels ranged from 0 to 5 IU/g OD. The results are summarized in FIG. 9. Color removal by the xylanases from *S. roseiscleroticus* is essentially linear with enzyme dose up to about 3 IU/g OD of pulp thereby indicating that the enzyme, and not some other factor, is responsible for color release.

We analyzed the ability of other xylanases to release chromophores. In a direct comparison of several xylanase preparations when each was tested at the same loading rate on pulp, the *S. roseiscleroticus* xylanases removed significant amounts of color, whereas the xylanase preparations from *Trichoderma reesei*, and *Aureobasidium pullulans* did not. No other fungal xylanase we analyzed released chromophores.

Figure 10:
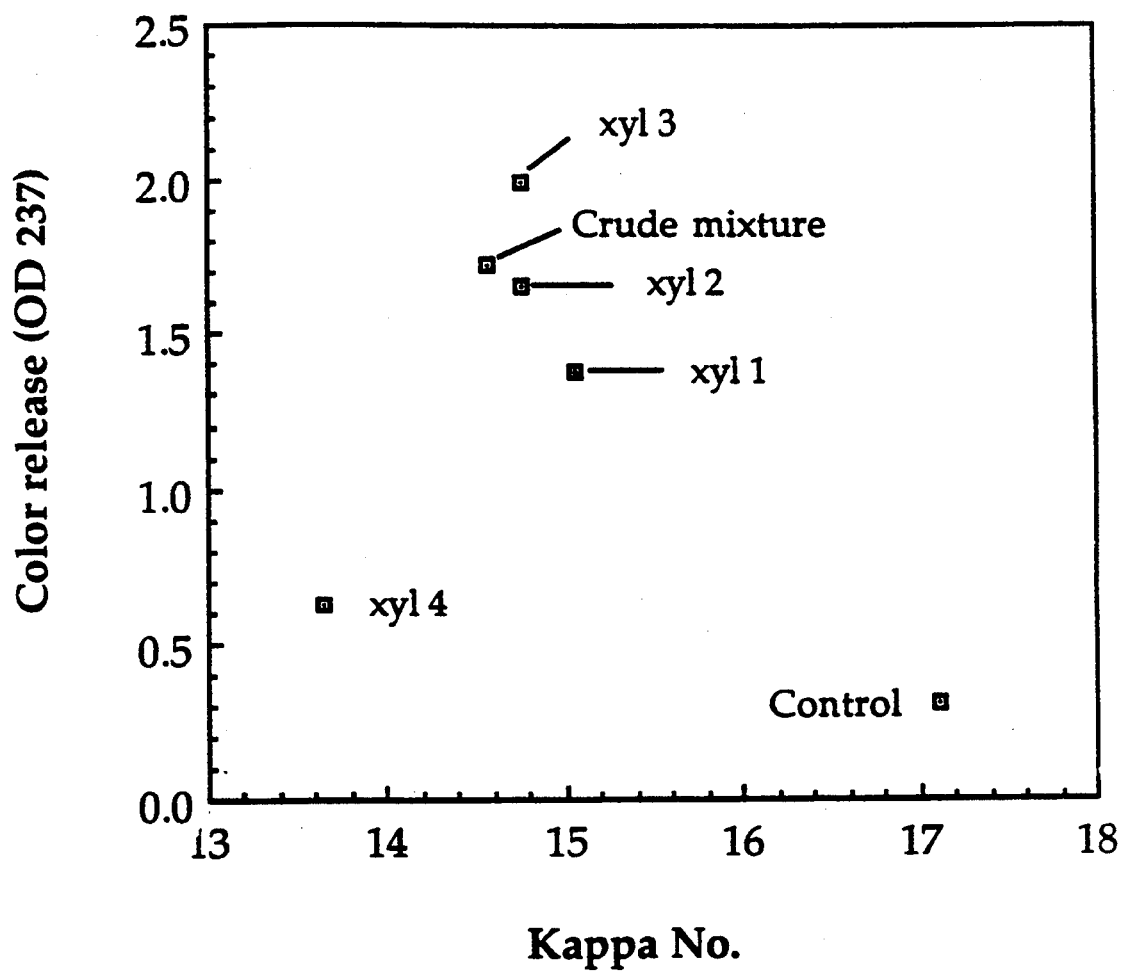
FIG. 10 is a diagram comparing chromophore release, as measured by absorbance at 237 nm, versus resulting kappa number of the pulp after extraction with alkali for the four different xylanases and the xylanase mixture.

At least two of the xylanase fractions were able to release color when acting alone. Samples of southern red oak kraft pulp were treated with 5 IU/g OD of purified xylanase isoenzyme fractions under conditions employed above. The release of chromophores was determined by spectroscopy at 237 nm, and the resulting kappa numbers of the pulps following extraction with 1% alkali at 65° C. for 1 hour were measured. For comparison, the color release and kappa number of a control pulp not treated with enzyme is also shown. FIG. 10 describes these results.

FIG. 10 shows that xyl 4 results in a relatively greater reduction in kappa per unit of enzyme activity employed and that xyl 3 results in relatively greater release of color. As is shown in FIG. 10, 5 IU/g of xyl 3 alone was able to release even more color than the mixture of xylanases when applied at the same dosing level. Some color was released by the buffer alone, but this was significantly less than that released by the enzymes.

The xylanases of the present invention are capable of releasing chromophores from secondary fiber pulps.

We used the xylanases to enhance color removal and kappa reduction of old corrugated containers prepared from softwood secondary fiber. A pulp with an initial kappa of 86 was prepared from old corrugated containers (OCC) and divided into two batches. One batch was soaked in alkali (10%, OD pulp basis) at room temperature for 4 hours; the other batch was used without further treatment. The control OCC and the alkali-treated OCC were each treated with 5 IU of xylanase/g OD pulp under the standard conditions, and the resulting supernatant solutions were recovered and assayed for absorbancies at 237 and 280 nm. Effectiveness was determined by multiplying the volume of the solution times the absorbancy at each wavelength (optical density ml=OD units). FIG. 11 graphically illustrates the results. As seen in FIG. 11, the enzyme treatment was particularly effective in removing chromophores absorbing at 237 nm.

Figure 12:
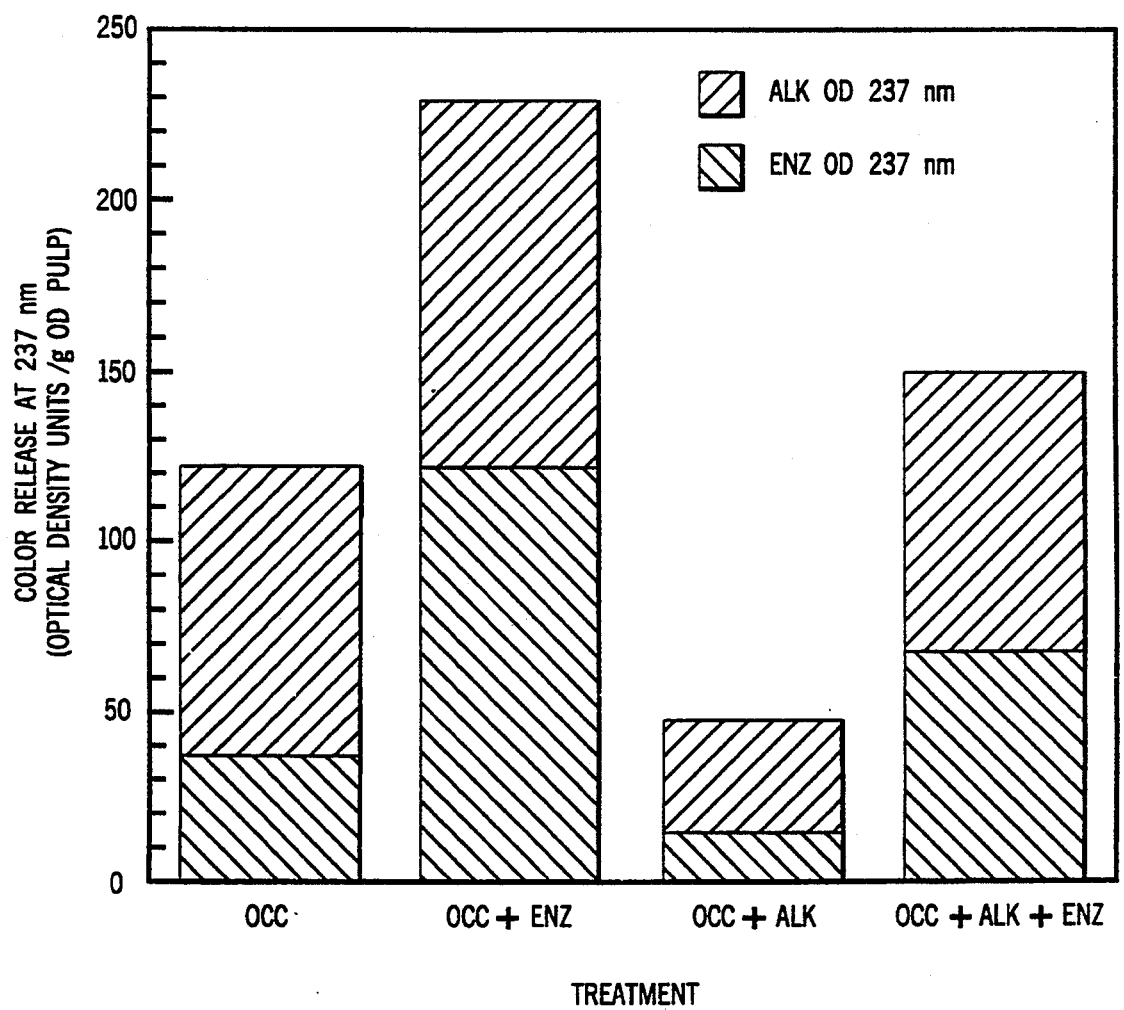
FIG. 12 is a diagram comparing chromophore release and various pulping treatments involving old corrugated containers and alkali extraction.

Enzyme treatment also facilitated the subsequent extraction of chromophores by 1% alkali as is shown in FIG. 12. Notably, enzyme treatment enhanced 1% alkali extraction of material absorbing at 237 nm even when the OCC had previously been subjected to extraction with 10% alkali. In all instances removal of chromophores was greater with enzyme treatment than without.

FIG. 12 illustrates chromophores released into solution from OCC by enzyme treatment alone (solid bars) or following extraction with 1% alkali (hatched bars). Referring to FIG. 12, OCC=Old corrugated containers; OCC+Enz=pulp that had been treated with enzyme prior to extraction with 1% alkali; OCC+Alk=OCC that had been treated with 10% alkali prior to a second extraction with 1% alkali; OCC+ Alk+Enz=OCC that had been treated with 10% alkali, followed by enzyme treatment, followed by extraction with 1% alkali.

Figure 13:
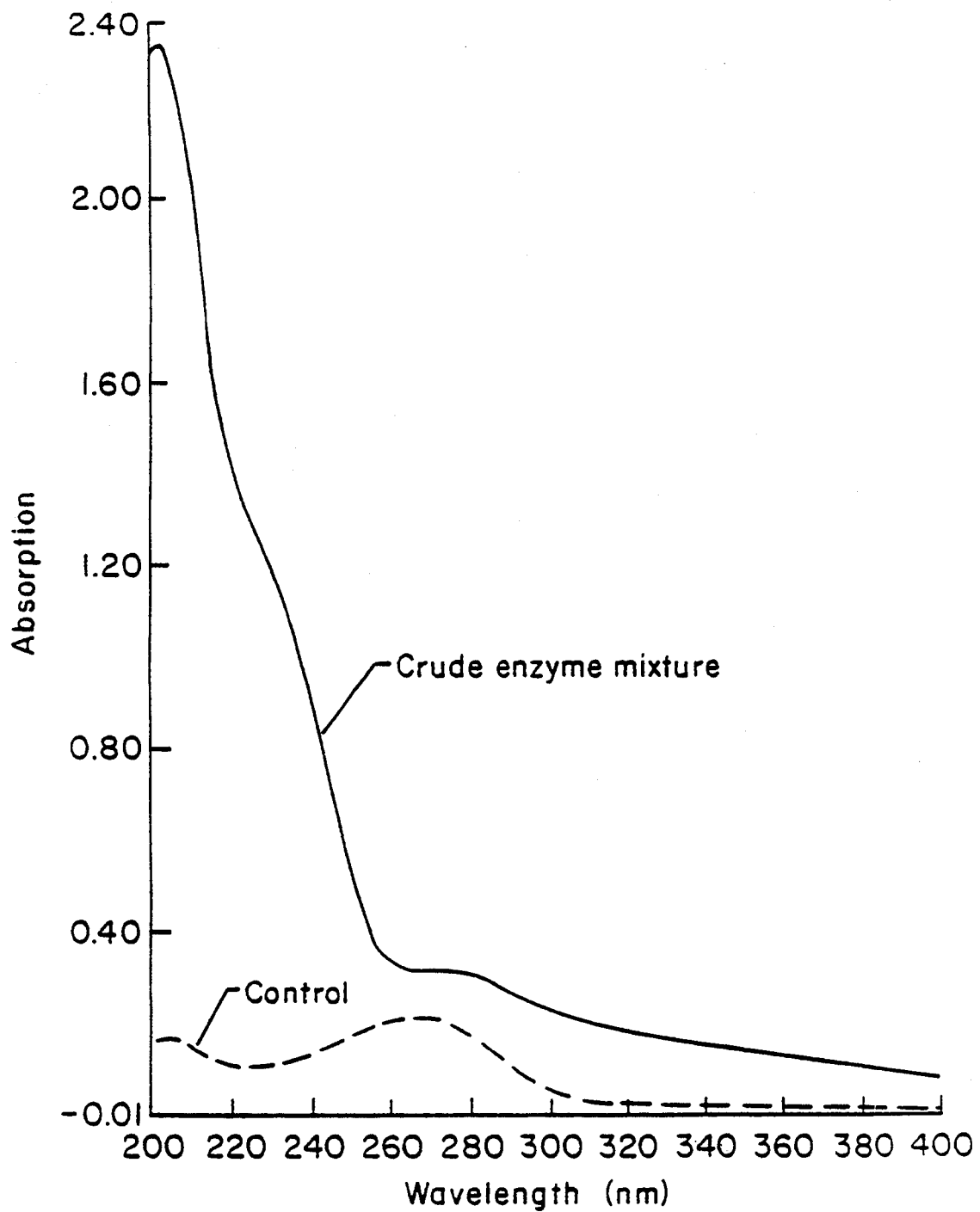
FIG. 13 is an absorption spectrum of the colored material removed by the xylanases compared to the absorption spectrum of material removed by buffer alone.

We have partially characterized the nature of the chromophores by UV/visible spectroscopy. The absorption spectrum of the chromophores does not correspond to a characteristic spectrum for lignin, i.e. there is no absorption peak at 280 nm (FIG. 13).

Figure 14A:
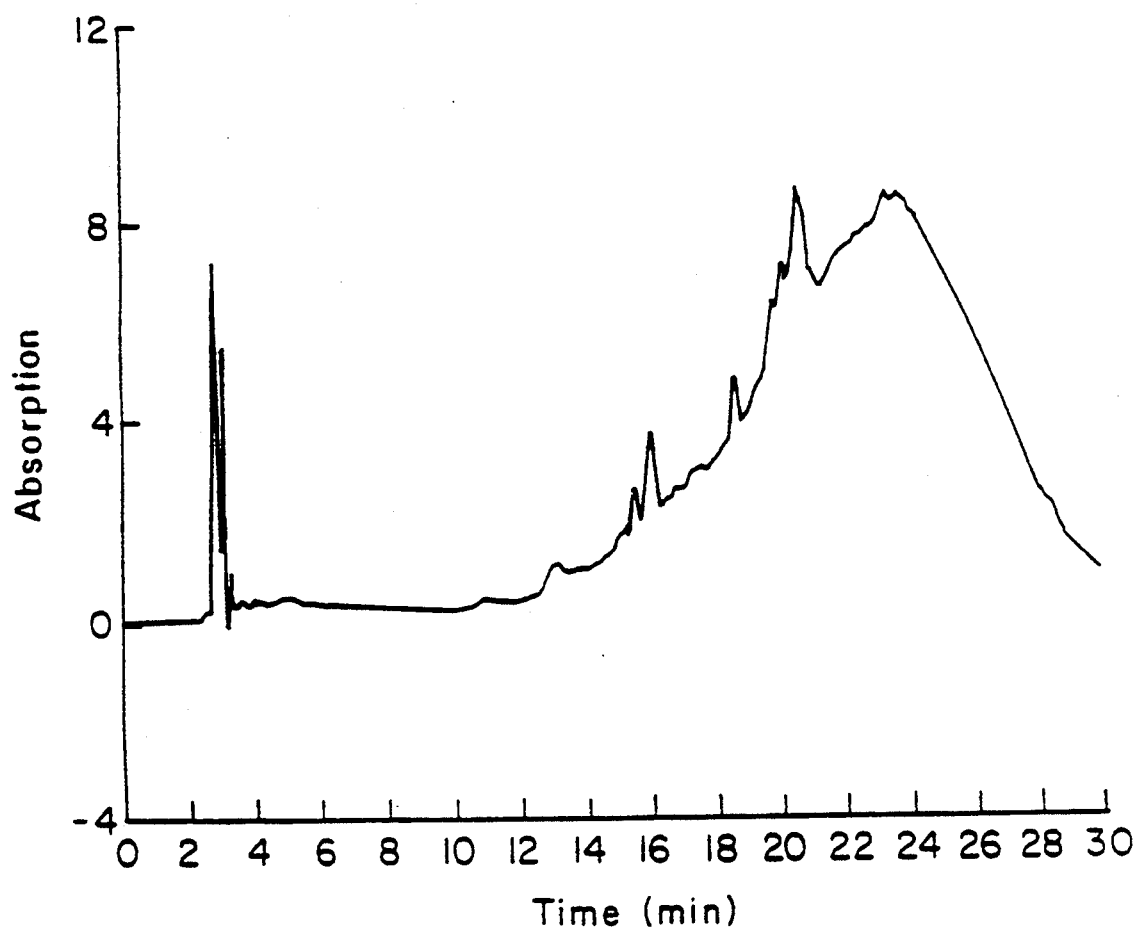
FIG. 14 (A) and (B) illustrates the absorbance of the chromophores in the ultraviolet (B) and visible regions (A) following their separation by reverse phase liquid chromatography.
Figure 14B:
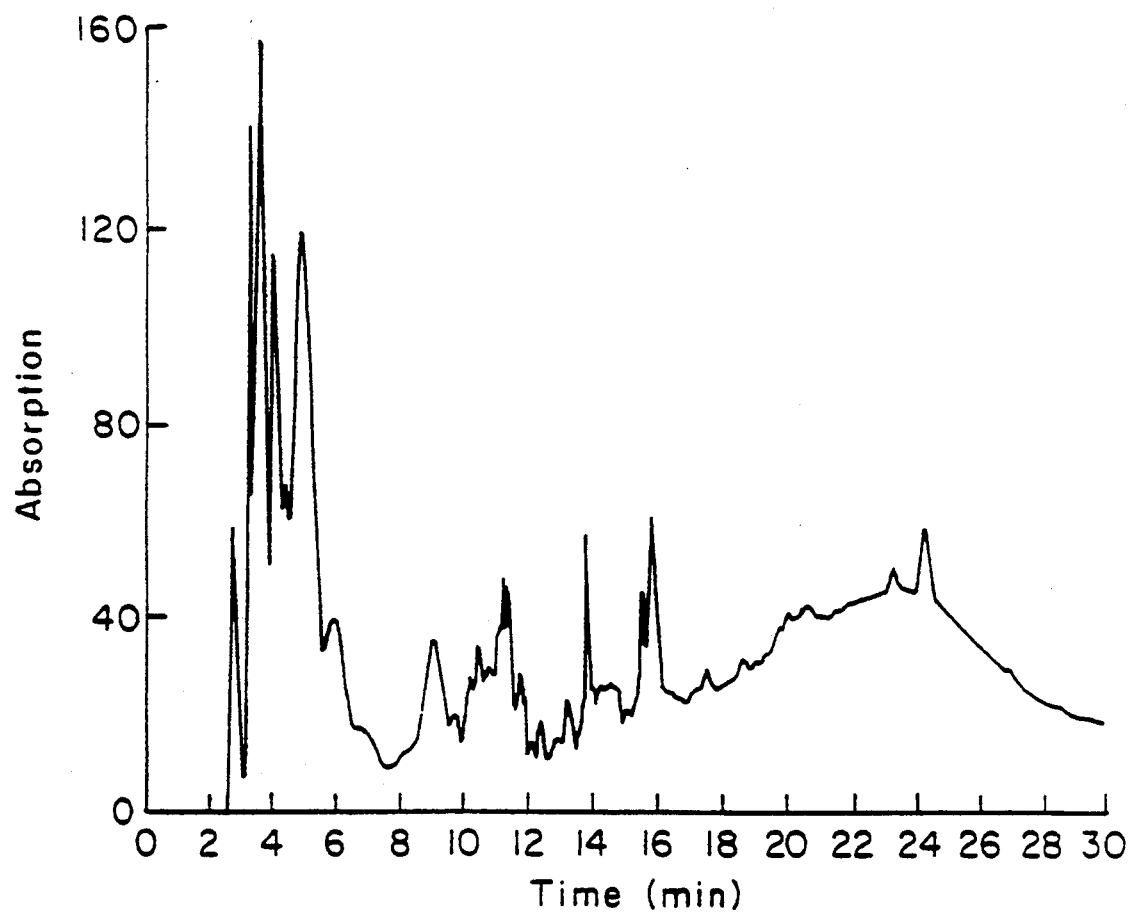
Figure 15A:
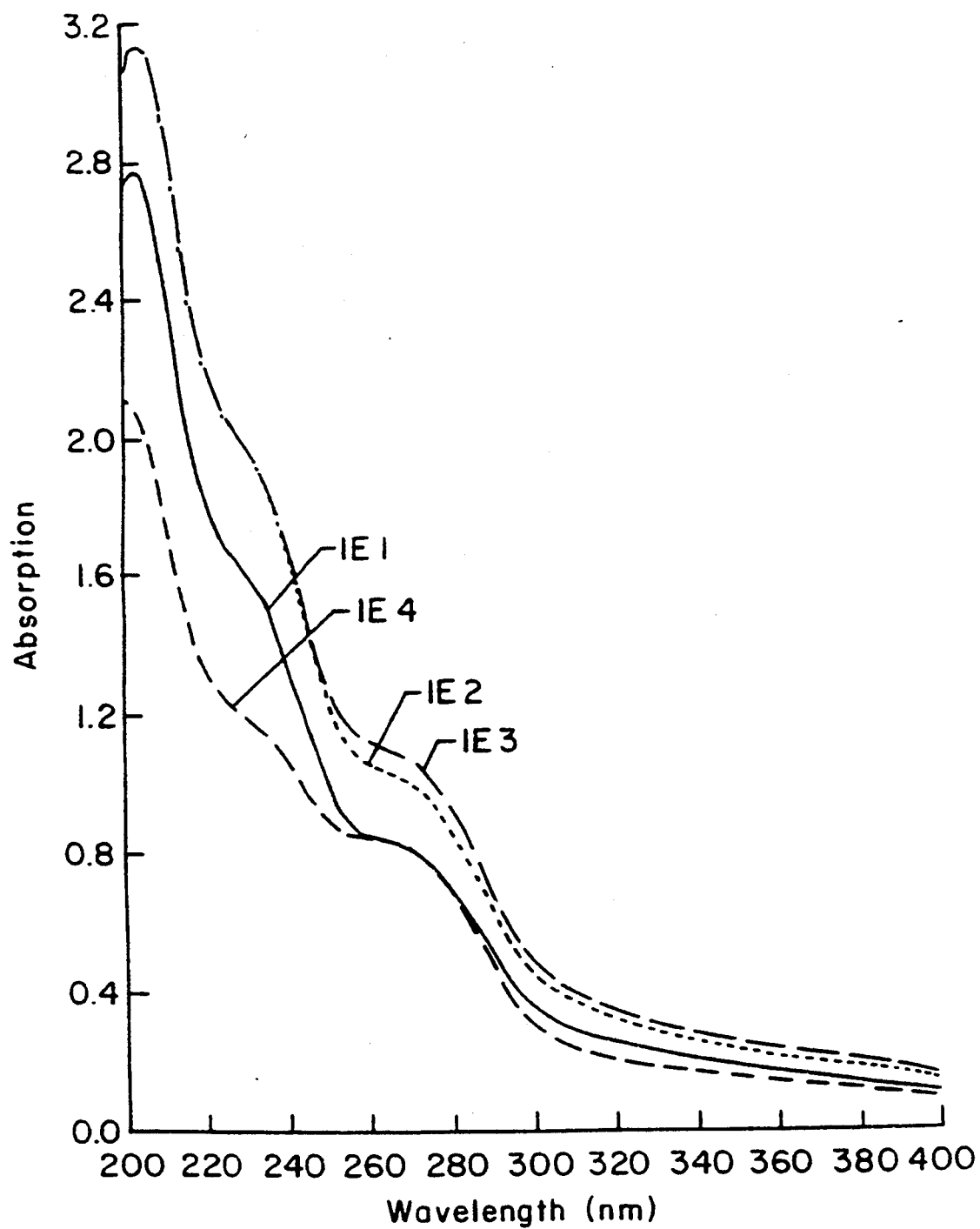
FIG. 15 (A) and (B) are UV spectra of chromophores released during enzymatic treatment (A) and following alkali extraction (B).
Figure 15B:
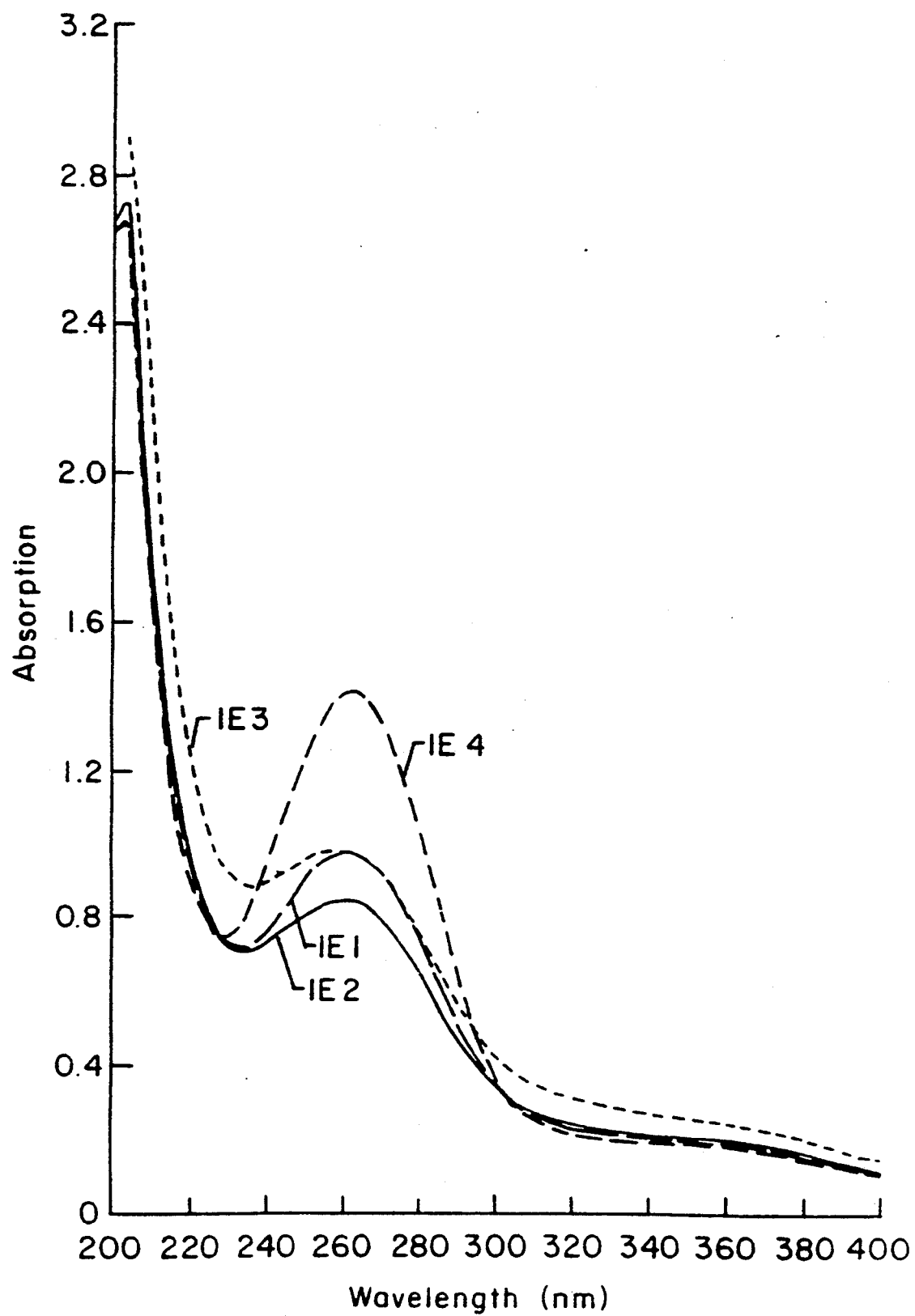

We also fractionated the chromophores using a reverse-phase HPLC column that separates the products on the basis of their hydrophobicity. The most hydrophobic compounds are eluted last under the conditions of this separation. We employed a diode array detector to determine the adsorption characteristics of each product peak as it emerged from the column. Two broad-band adsorptions were employed: one in the UV region and one in the visible region. A total of more than 40 product peaks were observed. (FIG. 14) Strong UV adsorption was observed in most of the peaks, but especially in products eluting near the start of the run (more hydrophilic materials). Many fewer products were observed to absorb in the visible region. Most of these were more hydrophobic, i.e., they eluted later. FIG. 15 illustrates the UV spectra of chromophores released during enzymatic digestion (A) and following alkali extraction (B).

6. Identification of Other Xylanases Capable of Removing Chromophores

Several novel xylanase isolates were obtained and screened in the manner described above. The enzymatic activities were compared with *Streptomyces roseiscleroticus*. Other unidentified isolates were obtained from a culture collection (Dr. Goerge Szakacs, Technical University of Budapest, Budapest, Hungary). The Enzymes were compared for pH optima, pH stability and temperature stability. Results with the best isolate from our screening program, which we named J2-5, and with three thermophilic Actinomycetales from the Budapest collection (B-236, B228 and B-12-2) are described below.

Figure 16:
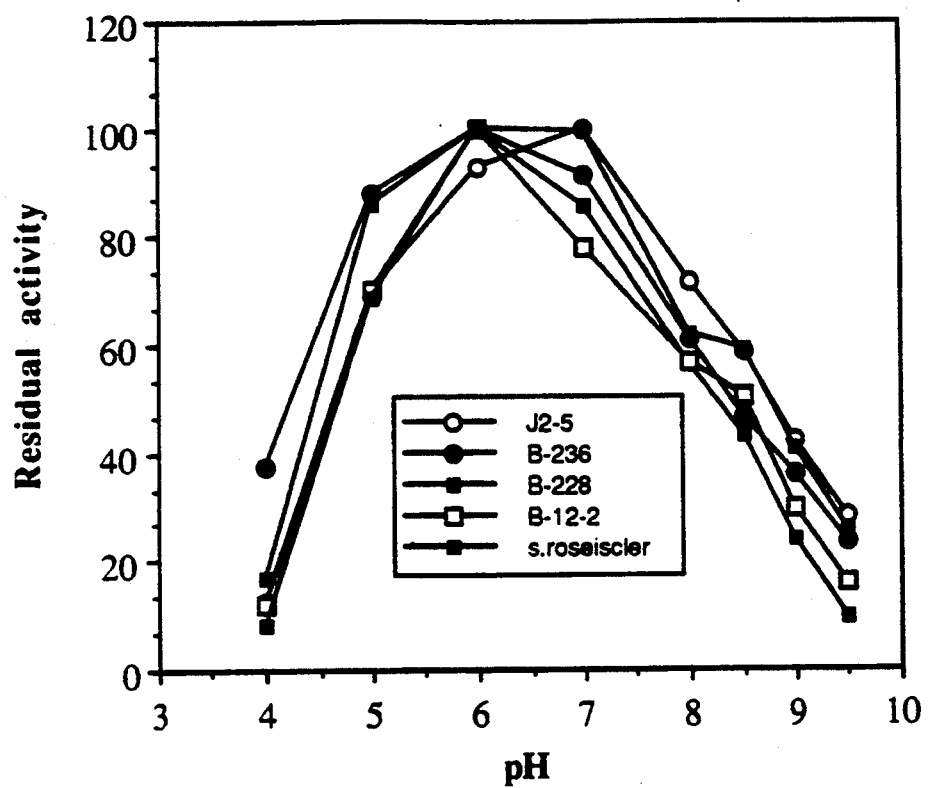
FIG. 16 is a diagram comparing the pH optimum of different crude xylanase preparations.

We consider a xylanase to have an alkaline pH activity if at least 10% of the enzyme activity is present at pH 9. As can be seen from FIG. 16, about 40% of the activity present at the optimum pH with the crude xylanases from J2-5 and *S. roseiscleroticus* had about 40% of their residual activity at pH 9. Xylanases from B-236, B-228 and B-12-2 had relatively less activity at this pH, but still had alkaline pH activity.

Figure 17A:
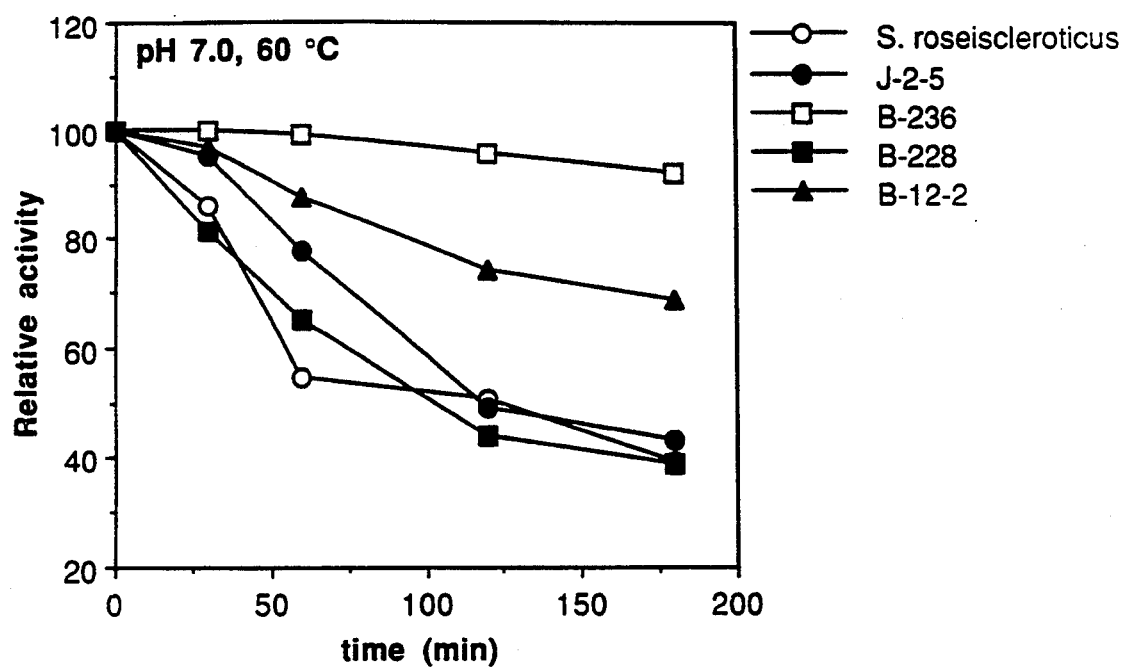
FIG. 17 (A), (B) and (C) is a set of three diagrams comparing the stability of different xylanase preparations at pH 7.0, 60° C.; pH 8.5, 60° C.; and pH 7.0, 65° C.
Figure 17B:
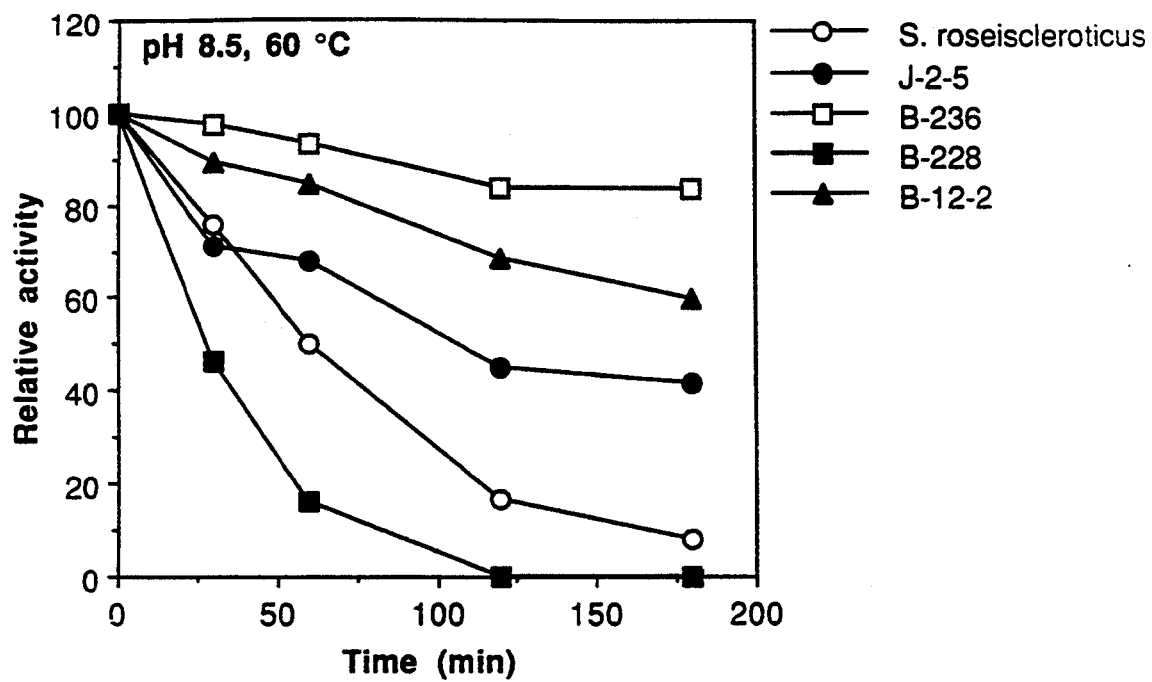
Figure 17C:
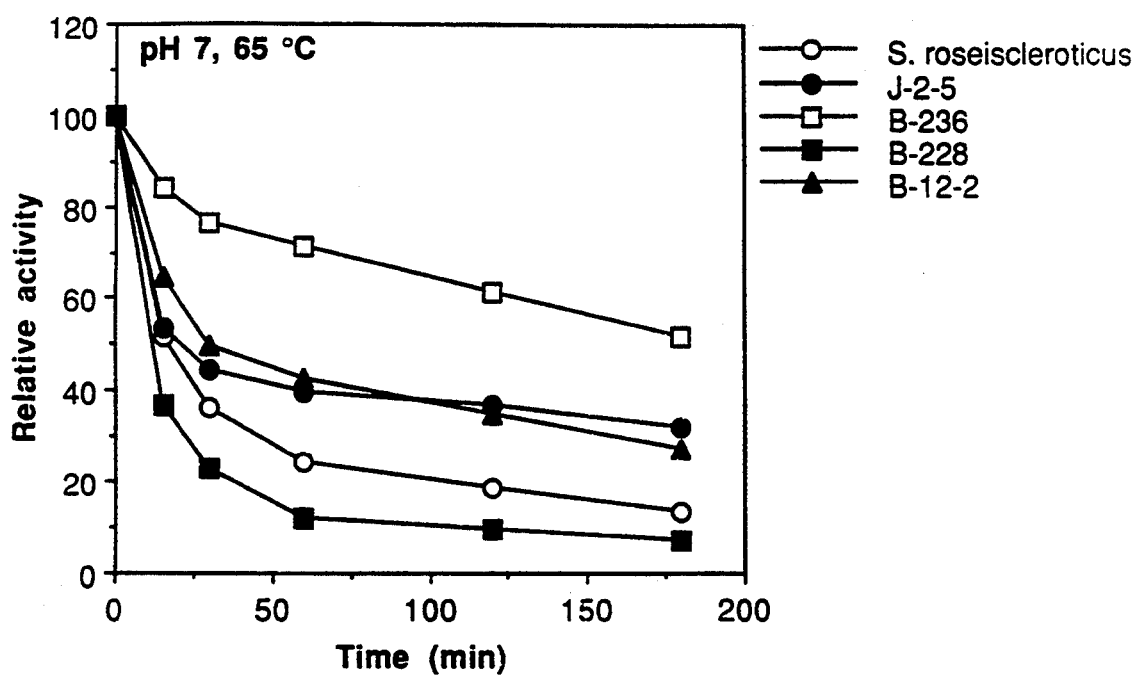

An enzyme should have thermal stability at an alkaline pH in order to operate at best advantage under the conditions described. Therefore, we tested the thermal stability (at 60° C.) of these preparations at pH 7.0 and 8.5. As can be seen in FIG. 17 (a, b, c), the xylanase preparation from B-236 showed good stability at 60° C. at both pH 7.0 and 8.5. In both instances, the second-most stable enzyme was from B-12-2. As can also be noted from FIG. 17, B-236 showed acceptable thermal stability even at 65° C., pH 7.0.

Figure 18:
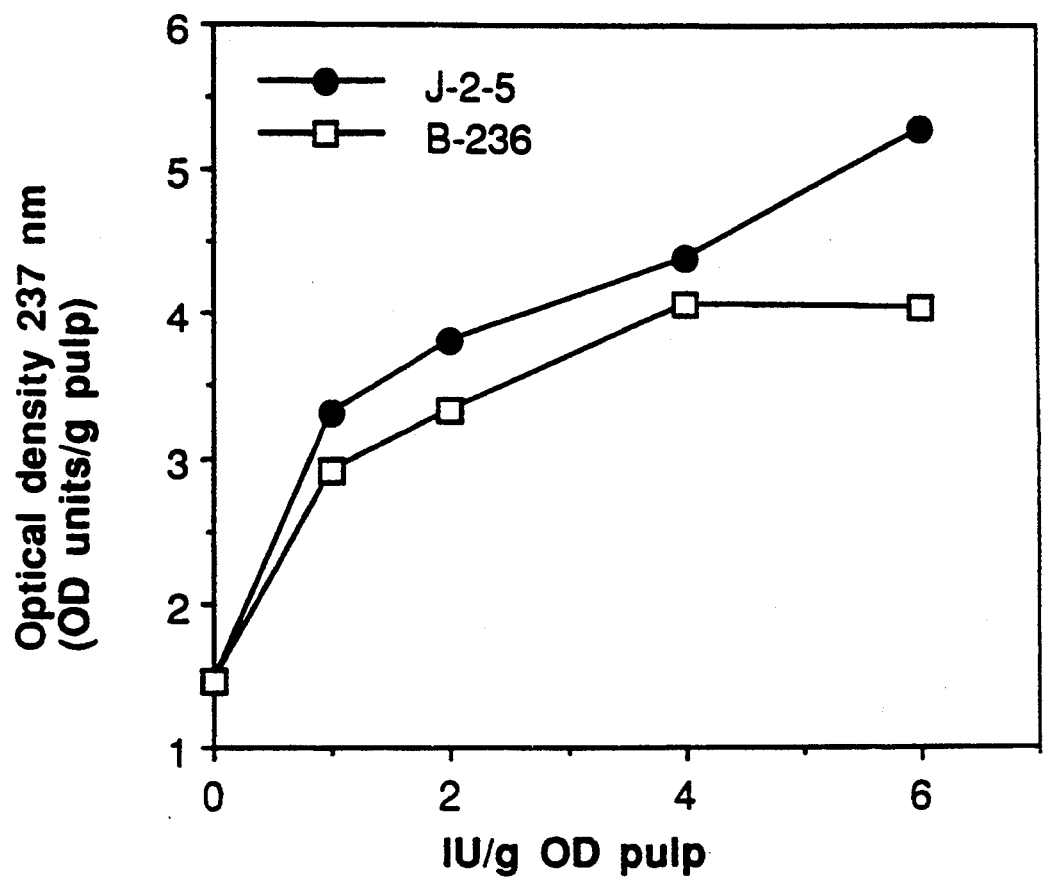
FIG. 18 is a diagram comparing chromophore release from two different xylanase preparations.

Crude enzyme preparations from J2-5 and B-236 were compared for their abilities to release chromophores at pH 7.0, 60° C. The results are shown in FIG. 18. As can be observed, both preparations were able to release chromophores from a softwood pulp. The enzyme from J2-5 was slightly more effective than that from B-236.

Enzymes J2-5, B-236 and B-12-2 were compared as to their ability to reduce kappa and release chromophores as a function of increasing enzyme amount. The following table summarizes the color release and the kappa number following alkali extraction of softwood kraft pulp. In this particular instance, 10% alkali was used rather than the 1% alkali used previously. All other conditions for color release were the same as above.

TABLE 5

| Enzymes | kappa number | % decrease | Color release Abs 237 nm/g OD |
|---|---|---|---|
| Control (buffer) | 14.7 | | 14.6 |
| J2-5 xylanase | | | |
| 1 IU/g OD pulp | 12.3 | 16.3 | 33.1 |
| 2 | 12.5 | 15.0 | 38.0 |
| 4 | 13.3 | 9.5 | 43.9 |
| 6 | 11.4 | 22.5 | 52.9 |
| B-236 xylanase | | | |
| 1 | 12.5 | 15.0 | 29.1 |
| 2 | 12.7 | 13.6 | 33.3 |
| 4 | 12.5 | 15.0 | 40.6 |
| 6 | 11.5 | 21.8 | 40.5 |
| B-12-2 xylanase 6 | 10.5 | 28.5 | 54.7 |

We claim:

1. A substantially pure preparation of xyl 3 obtained from *Streptomyces roseiscleroticus* NRRL B-11019, wherein xyl 3 has a molecular weight of approximately 21 kD as determined by SDS-gel electrophoresis and a pH optima of pH 5-pH 7.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 53 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: streptomyces roseiscleroticus
    ( B ) STRAIN: NRRLB-11019

( x i ) SEQUENCE DESCRIPTION: SEQ ID NO:1:

```
Cys Met Ser Trp Arg Asp Asn Arg Met Ala Leu Ser Thr Tyr Lys Tyr
 1           5                       10                      15
Cys Glu Arg Ala Leu Ala Glu Ser Thr Leu Gly Ala Ala Ala Ala Gln
             20                  25                  30
Ser Gly Arg Tyr Phe Gly Thr Ala Ile Ala Ala Gly Arg Leu Gly Met
             35                  40                  45
Met Met Ile Ile Ile
             50
```

( 2 ) INFORMATION FOR SEQ ID NO:2:

( i ) SEQUENCE CHARACTERISTICS:
    ( A ) LENGTH: 54 amino acids ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
                    ( A ) ORGANISM: streptomyces roseiscleroticus
                    ( B ) STRAIN: NRRLB-11019

( x i ) SEQUENCE DESCRIPTION: SEQ ID NO:2:

Cys Met Ser Trp Arg Asp Asn Arg Met Ala Leu Ser Thr Tyr Lys Tyr
1               5                   10                  15

Cys Glu Arg Ala Leu Xaa Thr Val Val Thr Thr Asn Gln Thr Gly Thr
                20              25                  30

His Glu Gly Tyr Tyr Tyr Ser Phe Xaa Thr Asp Ala Pro Asn Asp Ser
            35              40              45

Thr Tyr Met Met Ile Ile
        50

( 2 ) INFORMATION FOR SEQ ID NO:3:

( i ) SEQUENCE CHARACTERISTICS:
                    ( A ) LENGTH: 56 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
                    ( A ) ORGANISM: streptomyces roseiscleroticus
                    ( B ) STRAIN: NRRLB-11019

( x i ) SEQUENCE DESCRIPTION: SEQ ID NO:3:

Cys Met Ser Trp Arg Asp Asn Arg Met Ala Leu Ser Thr Tyr Lys Tyr
1               5                   10                  15

Cys Glu Arg Ala Leu Ala Thr Thr Ile Thr Thr Asn Gln Thr Gly Tyr
                20              25                  30

Asp Gly Met Tyr Tyr Ser Phe Trp Thr Asp Gly Xaa Xaa Ser Val Xaa
            35              40              45

Met Thr Leu Asn Xaa Gly Met Ile
        50              55

( 2 ) INFORMATION FOR SEQ ID NO:4:

( i ) SEQUENCE CHARACTERISTICS:
                    ( A ) LENGTH: 50 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal (v i) ORIGINAL SOURCE:
    (A) ORGANISM: streptomyces roseiscleroticus
    (B) STRAIN: NRRLB-11019

(x i) SEQUENCE DESCRIPTION: SEQ ID NO:4:

| Cys | Met | Ser | Trp | Arg | Asp | Asn | Arg | Met | Ala | Leu | Ser | Thr | Tyr | Lys | Tyr |
|---|---|---|---|---|---|---|---|---|---|---|---|---|---|---|---|
| 1 | | | | 5 | | | | 10 | | | | | | 15 | |
| Cys | Glu | Arg | Ala | Leu | Ala | Glu | Ser | Thr | Leu | Gly | Ala | Ala | Ala | Gln | Gln |
| | | | 20 | | | | | 25 | | | | | 30 | | |
| Ser | Gly | Tyr | Tyr | Phe | Gly | Thr | Ala | Ile | Ala | Ala | Gly | Leu | Leu | Met | Met |
| | | | 35 | | | | 40 | | | | | 45 | | | |
| Ile | Ile | | | | | | | | | | | | | | |
| | 50 | | | | | | | | | | | | | | |